US006835818B2

(12) United States Patent
Schlievert et al.

(10) Patent No.: US 6,835,818 B2
(45) Date of Patent: *Dec. 28, 2004

(54) MUTANTS OF STREPTOCOCCAL TOXIN C AND METHODS OF USE

(75) Inventors: Patrick M. Schlievert, Edina, MN (US); Douglas Ohlendorf, Eden Prairie, MN (US); David T. Mitchell, Vadnais Heights, MN (US); Pamala J. Gahr, Woodbury, MN (US)

(73) Assignee: Regents of the University of Minnesota, Minneapolis, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/308,829

(22) PCT Filed: Dec. 5, 1997

(86) PCT No.: PCT/US97/22125

§ 371 (c)(1),
(2), (4) Date: Jul. 14, 1999

(87) PCT Pub. No.: WO98/24910

PCT Pub. Date: Jun. 11, 1998

(65) Prior Publication Data

US 2002/0039585 A1 Apr. 4, 2002

Related U.S. Application Data

(60) Provisional application No. 60/033,251, filed on Dec. 6, 1996.

(51) Int. Cl.[7] .......................... A01N 63/00; A61K 39/40; A61K 39/02; A61K 39/44; A61K 39/38

(52) U.S. Cl. ................ 530/388.4; 424/93.44; 424/165.1; 424/183.1; 424/184.1; 424/190.1; 424/200.1; 424/203.1; 424/236.1; 424/237.1; 424/244.1; 424/832; 435/7.31; 435/7.34; 435/36; 435/69.3; 435/253.4; 435/340; 530/388.4; 930/200

(58) Field of Search ..................... 424/93.44, 165.1, 424/200.1, 203.1, 236.1, 237.1, 244.1, 832; 435/7.34, 36, 253.4, 340; 530/388.4

(56) References Cited

U.S. PATENT DOCUMENTS

| 5,298,396 A | 3/1994 | Kotzin et al. |
| 5,336,598 A | 8/1994 | Kotzin et al. |
| 5,460,813 A | * 10/1995 | Leung et al. ............ 424/115 |

FOREIGN PATENT DOCUMENTS

| WO | WO 85/00832 | 2/1985 |
| WO | WO 93/14634 | 8/1993 |
| WO | WO 96/40930 A | 12/1996 |

OTHER PUBLICATIONS

Hartwig et al. International Immunology. vol. 5, No. 8. pp. 869–875, 1993.*

(List continued on next page.)

Primary Examiner—Lynette R. F. Smith
Assistant Examiner—J. Hines
(74) Attorney, Agent, or Firm—Merchant & Gould P.C.

(57) ABSTRACT

This invention is directed to mutant SPE-C toxins or fragments thereof, vaccine and pharmaceutical compositions, and methods of using the vaccine and pharmaceutical compositions. The preferred SPE-C toxin has at least one amino acid change and is substantially non-lethal compared with the wild type SPE-C toxin. The mutant SPE-C toxins can form vaccine compositions useful to protect animals against the biological activities of wild type SPE-C toxin.

21 Claims, 10 Drawing Sheets

OTHER PUBLICATIONS

Goshorn et al. 1998. Mol. Gen. Genet. 212:66–70, 1988.*
Goshorn et al. 1988. Infect. and Immun. 56(9): 2518–2520, 1988.*
Hovde et al. 1994. Mol. Micro. 1994. 13(5): 897–909, 1994.*
Kline et al. 1996. Infect. and Immun. 64(3): 861–869, 1996.*
Norby–Teglund et al. J. of Clin. Micro. 32(3): 705–709, 1994.*
Black, C.M. et al., "Detection of Streptococcal Pyrogenic Exotoxin Genes by a Nested Polymerase Chain Reaction", *Molecular and Cellular Probes*, vol. 7, pp. 255–259 (1993).
Murray, D. et al., "Immunobiologic and Biochemical Properties of Mutants of Toxic Shock Syndrome Toxin–1", J. Immunol (US) (1994) 152(1):87–95.
Musser et al., "Streptococcus Pyogenes Causing Toxic Shock–like Syndrome and Other Invasive Diseases: Colonal Diversity and Pyrogenic Exotoxin Expression", Proc. Nat'l. Acad. Sci. (USA) 88:2668–2672 (1991).
Musser, J. et al., "Infect Immun", Mar. 1995, 63(3) P994–1003.
Norrby–Teglund, A. et al., "Detection and Nucleotide Sequence Analysis of the speC Gene in Swedish Clinical Group A Streptococcal Isolates", Journal of Clinical Microbiology, 32(3):705–709 (Mar. 1994).
Norrby–Teglund, A. et al., "Relation between Low Capacity of Human Sera to Inhibit Streptococcal Mitogenes and Serious Manifestation of Disease", J. Infect. Dis. 170:585–91 (1994).
Perrin, S. et al., "Site–specific mutagenesis using asymmetric polymerase chain reaction and a single mutant primer", Nucleic Acids Research 18:7433–7438 (1990).
Prasad, G. et al., "Structure of Toxic Shock Syndrome Toxine 1", Biochemistry vol. 32, No. 50 (Dec. 21, 1993) 50:13761–13766.
Rennell, D. et al, "Systematic Mutation of Bacteriophage T4 Lysozyme", J. Mol. Biol. 222:67–87 (1991).
Revie, D., et al., "Kinetic analysis for optimization of DNA ligation reactions", Nucleic Acids Research 16:10301–10321 (1988).
Roggiani, A. et al., "Localization of biological activities of Streptococcal Pyrogenic Exotoxin", poster presentation at the ASM 94$^{th}$ General Meeting, Las Vegas, Nevada (1994).
Roggiani, M. et al., "Analysis of Toxicity of Streptococcal Pyrogenic Exotoxin A Mutants", Infection and Immunity, 65(7):2868–2875 (Jul. 1997).
Schlievert et al., "Group B Streptococcal Toxic Shock–Like Syndrome: Report of a Case and Purification of Associated Pyrogenic Toxin", Clin. Infect. Dis. 17:26–31 (1993).
Schlievert, "Role of Superantigens in Human Disease", J. Infect. Dis. 167:997–1002 (1993).
Schlievert, P. et al., "Infect Immun", Jun. 1989, 57 (6) P1865–7.
Scott et al., Characterization of *Staphylcoccus aureus* Isolates from Patients with Toxic Shock Syndrome, Using Polyethylene Infection Chambers in Rabbits, Infection and Immunity 39:383–387 (Jan. 1983).
Swaminathan, "Crystal Structure of Staphococcal Enterotoxin B as Superantigen", Nature 359:801–806 (1992).
Tomai, M. et al., "District T–Cell Receptor Vβ Gene Usage T. Lymphocytes Stimulated with the Streptococcal Pyrogenic Exotoxins and pep M5 Protein", Infection and Immunity 60:701–705 (Feb. 1992).

Wallace, C., Understanding cytochrome c function: engineering protein structure by semisynthesis, FASEB Journal 7:505–515 (1993).
Weeks et al., "Nucleotide Sequence of the Type A Streptococcal Exotoxin (Erythrogenic Toxin) Gene from *Streptococcus pyrogenes* Bacteriophage T12", Infection and Immunology, Apr. 1987, 52:144–150, pp. 144–150.
Acharya, K. et al., "Structural Basis of Superantigen Action Inferred from Crystal Structure of Toxic–Shock Syndrome Toxin–1", Nature 367:94–97 (1994).
Aiyar, A. et al., "Modification of the Megaprimer Method of PCR Mutagenesis: Improved Amplification of the Final Product", BioTechniques vol. 14, No. 3 (1993) pp. 366–369.
Altschyl, S. et al., "Optimal Sequence Alignment Using Affine Gap Costs", Bulletin of Math. Biol. 48:603–616 (1986).
Anthony–Cahill, S. et al., "Site–specific mutagenesis with unnatural amino acids", Trends in Biochem. Sci. 14:400–403 (1989).
Barsumian et al., "Nonspecific and Specific Immunological Mitogenicity by Group A Streptococcal Pyrogenic Exotoxins", Infection and Immunity 22:681–688 (1978).
Belani, K. et al., Association of exotoxin–producing Group A streptococci and severe disease in children, Pediatr. Infect. Dis. J. 10:351–354 (1991).
Betley et al., "Staphylcoccal Enterotoxins, Toxic Shock Syndrome Toxin and Streptococcal Pyrogenic Exotoxins: A Comparative Study of their Molecuar Biology", Chem. Immun. 55:1–35 (1992).
Birkhaug et al., "Studies in Scarlet Fever II: Studies on the Use of Convalescent Scarlet Fever Serum in Dochez Scarletino Antistreptococcic serum for the treatment of scarlet fever", Bull. John Hopkins Hosp. 36:134–171 (1925).
Bohach et al., "Staphylcoccal and Streptococcal Pyrogenic Toxins Involved in Toxic Shock Syndrome and Related Illnesses", Crit. Rev. Microbiol. 17:251–272 (1989).
Bowie, J. et al., "Deciphering the Message in Protein Sequences: Tolerance to Amino Acid Substitutions", Science 247:1306–1310. (Mar. 16, 1990).
Braunstein, N. et al., "Sequences in Both Class II Major Histomcompatibility Complex a and β Chains Contribute to the Binding of the Superantigen Toxic Shock Syndrome Toxin 1", J. Exper. Med. 175:1301–1305 (Apr. 1, 1992).
Dohlsten et al., "Superantigen Induced Cytokines Supress Growth of Human Colon Carcinoma Cells", Int. J. Cancer 54:482–488 (1993).
Fast, D. et al., "Toxic Shock Syndrome–Associated Staphylcoccal and Streptococcal Pyrogenic Toxins are Potent Inducers of Tumor Necrosis Factor Production", Infection and Immunity 57:291–295 (Jan. 1989).
Goshorn, S. et al., "Cloning and characterization of the gene, speC, for pyrogenic exotoxin type C from Streptococcus pyogenes", Mol. Gen. Genet. 212:66–70 (1988).
Goshorn, S. et al., "Nucleotide Sequence of Streptococcal Pyrogenic Exotoxin Type C", Infection and Immunity 56:2518–2520 (1988).
Griggs, N. et al., "Mapping of Multiple Binding Domains of the Superantigen Staphylococcal Enterotoxin A for HLA", J. Immunology 148:2516–2521 (Apr. 15, 1992).
Hartwig, U. et al., 1993. "Mutations affecting MHC class II binding of the superantigen streptococcal erythrogenic toxin A." International Immunology 5(8):869–875.
Hattori, M. et al., "Structure of the rat $\alpha_2$–macroglobulin–coding gene", Gene 77:333–340 (1989).

Hauser, A. et al., "Molecular Analysis of Pyrogenic Exotoxins from *Streptococcus pyogenes* Isolates Associated with Toxic Shock–Like Syndrome", J. Clin. Microbiol. 29:1562–1567 (Aug. 1991).

Hedlund et al., "Superantigen–Based Tumor Therapy in Vivo Activation of Cytotoxic T Cells", Cancer Immun. Immunother. 36:89–93 (1993).

Hovde C. J. et al., "Investigation of the role of the disulphide bond in the activity and structure of staphylococcal enterotoxin C1", Molecular Microbiology, 13(5):897–909 (1994).

Hsiao, Ku–chuan et al., "A Fast and simple procedure for sequencing double stranded DNA with Seqenase", Nucleic Acids Research 19:2787 (1991).

Ihle et al., "Antibody Targeted Super Antigens Induce Lysis of Major Histocompatibility Complex Class II Negative T Cell Leukemia Lines", Cancer Res. 55:623–628 (1995).

Iwasaki et al., "Cloning, Characterization and Overexpression of *Streptococcus* Pyogenes Gene Encoding a New Type of Mitogenic Factor", FEBS Lett. 331:187–192 (1993).

Jardetzky, T. et al., "Three–dimensional structure of a human class II histocompatibility molecule complexed with superantigen", Nature 368:711–718 (Apr. 21, 1994).

Jett et al., "Identification of Staphylcoccal Enerotoxin B Sequences Important for Induction of Lymphocyte Proliferation Using Synthetic Peptide Fragments of the Toxin", Infection and Immunity 62:408–3415 (1994).

Johnson, L. et al., "Group A streptococcal phage T12 carries the structural gene for pyrogenic exotoxin type A", Mol. Gen. Genet. 194:52–56 (1994).

Johnson, L.P. et al, "Streptococcal pyrogenic exotoxin type A (scarlet fever toxin) is related to *Staphylococcus aureus* enterotoxin B", Mol Gen Genet, 203:354–356 (May 1986).

Kappler, J. et al., "Mutations Defining Functional Regions of the Superantigen Staphylcoccal Enterotoxin B.", J. Exp. Med. 175:387–396 (Feb. 1992).

Kline, J. et al., "Analysis of the Superantigenic Activity of Mutant and Allelic Forms of Streptococcal Pyrogenic Exotoxin A", Infection and Immunity 64(3):861–869 (Mar 1996).

Lee, P. et al, "Effects of Staphylococcal Toxic Shock Syndrome Toxin 1 on Aortic Endothelial Cells", J. Infect. Dis. 164:711–9 (1991).

Lee, P. et al., "Fluid Replacement Protection of Rabbits Challenged Subcutanteously with Toxic Shock Syndrome Toxins", Infection and Immunity 59(3):879–884 (Mar. 1991).

Marrack, P. et al., "The Staphylcoccal Enterotoxins and Their Relatives", Science 248:705–711 (May 1990).

Martin, D., et al., Molecular Epidemiology of Group A *Streptococcus* M Type 1 Infections, J. Infect. Dis. 167:1112–7 (1993).

Mollick, J. et al., "Localization of a Site on Bacterial Superantigens That Determines T Cell Receptor β Chain Specificity", J. Exp. Med. 177:283–293 (Feb. 1993).

Mollick, J. "Novel Superantigen Isolated from Pathogenic Strains of *Streptococcus pyogenes* with Aminoterminal Homology to Staphylcoccal Enterotoxins B and C", J. Clin. Invest. 92:710–719 (Aug. 1993).

* cited by examiner

FIG. 1

```
                -35                                              -10
CAACCTTGACTATTTAAATGGAACTGCCACTCCTAAAAACTAAAATATAAATACA

TTTATAAAATTTCTAAATAAACAGAAATCTGATTTTTAACTACTTACTGCTATTT
                                        SD
CATGTATTCTCGTACGAGTAATACATTTAATTAAGGAGAAAAA  ATG AAA AAG    9
                                             MET Lys Lys
```

| | | | | | | | | | | | | |
|---|---|---|---|---|---|---|---|---|---|---|---|---|
| ATT | AAC | ATC | ATC | AAA | ATA | GTT | TTC | ATA | ATT | ACA | GTC | ATA | CTG | 51 |
| Ile | Asn | Ile | Ile | Lys | Ile | Val | Phe | Ile | Ile | Thr | Val | Ile | Leu | |
| ATT | TCT | ACT | TAT | TTC | ACC | TAT | CAT | CAA | AGT | *GAC | TCT | AAG | AAA | 93 |
| Ile | Ser | Thr | Tyr | Phe | Thr | Tyr | His | Gln | Ser | Asp | Ser | Lys | Lys | |
| GAC | ATT | TCG | AAT | GTT | AAA | AGT | GAT | TTA | CTT | TAT | GCA | TAC | ACT | 135 |
| Asp | Ile | Ser | Asn | Val | Lys | Ser | Asp | Leu | Leu | Tyr | Ala | Tyr | Thr | |
| ATA | ACT | CCT | TAT | GAT | TAT | AAA | GAT | TGC | AGG | GTA | AAT | TTT | TCA | 177 |
| Ile | Thr | Pro | Tyr | Asp | Tyr | Lys | Asp | Cys | Arg | Val | Asn | Phe | Ser | |
| ACG | ACA | CAC | ACA | TTA | AAC | ATT | GAT | ACT | CAA | AAA | TAT | AGA | GGG | 219 |
| Thr | Thr | His | Thr | Leu | Asn | Ile | Asp | Thr | Gln | Lys | Tyr | Arg | Gly | |
| AAA | GAC | TAT | TAT | ATT | AGT | TCC | GAA | ATG | TCT | TAT | GAG | GCC | TCT | 261 |
| Lys | Asp | Tyr | Tyr | Ile | Ser | Ser | Glu | MET | Ser | Tyr | Glu | Ala | Ser | |
| CAA | AAA | TTT | AAA | CGA | GAT | GAT | CAT | GTA | GAT | GTT | TTT | GGA | TTA | 303 |
| Gln | Lys | Phe | Lys | Arg | Asp | Asp | His | Val | Asp | Val | Phe | Gly | Leu | |
| TTT | TAT | ATT | CTT | AAT | TCT | CAC | ACC | GGT | GAG | TAC | ATC | TAT | GGA | 345 |
| Phe | Tyr | Ile | Leu | Asn | Ser | His | Thr | Gly | Glu | Tyr | Ile | Tyr | Gly | |
| GGA | ATT | ACG | CCT | GCT | CAA | AAT | AAT | AAA | GTA | AAT | CAT | AAA | TTA | 387 |
| Gly | Ile | Thr | Pro | Ala | Gln | Asn | Asn | Lys | Val | Asn | His | Lys | Leu | |
| TTG | GGA | AAT | CTA | TTT | ATT | TCG | GGA | GAA | TCT | CAA | CAG | AAC | TTA | 429 |
| Leu | Gly | Asn | Leu | Phe | Ile | Ser | Gly | Glu | Ser | Gln | Gln | Asn | Leu | |
| AAT | AAC | AAG | ATT | ATT | CTA | GAA | AAG | GAT | ATC | GTA | ACT | TTC | CAG | 471 |
| Asn | Asn | Lys | Ile | Ile | Leu | Glu | Lys | Asp | Ile | Val | Thr | Phe | Gln | |
| GAA | ATT | GAC | TTT | AAA | ATC | AGA | AAA | TAC | CTT | ATG | GAT | AAT | TAT | 513 |
| Glu | Ile | Asp | Phe | Lys | Ile | Arg | Lys | Tyr | Leu | MET | Asp | Asn | Tyr | |
| AAA | ATT | TAT | GAC | GCT | ACT | TCT | CCT | TAT | GTA | AGC | GGC | AGA | ATC | 555 |
| Lys | Ile | Tyr | Asp | Ala | Thr | Ser | Pro | Tyr | Val | Ser | Gly | Arg | Ile | |
| GAA | ATT | GGC | ACA | AAA | GAT | GGG | AAA | CAT | GAG | CAA | ATA | GAC | TTA | 597 |
| Glu | Ile | Gly | Thr | Lys | Asp | Gly | Lys | His | Glu | Gln | Ile | Asp | Leu | |
| TTT | GAC | TCA | CCA | AAT | GAA | GGG | ACT | AGA | TCA | GAT | ATT | TTT | GCA | 639 |
| Phe | Asp | Ser | Pro | Asn | Glu | Gly | Thr | Arg | Ser | Asp | Ile | Phe | Ala | |
| AAA | TAT | AAA | GAT | AAT | AGA | ATT | ATC | AAT | ATG | AAG | AAC | TTT | AGT | 681 |
| Lys | Tyr | Lys | Asp | Asn | Arg | Ile | Ile | Asn | MET | Lys | Asn | Phe | Ser | |

```
CAT TTC GAT ATT TAT CTT GAA AAA TAATTCATCATACACAAAAAACC
His Phe Asp Ile Tyr Leu Glu Lys TER
```

SPE C

SPE C

```
                    SEQUENCE LISTING

<160> NUMBER OF SEQ ID NOS: 2

<210> SEQ ID NO 1
<211> LENGTH: 936
<212> TYPE: DNA
<213> ORGANISM: Streptococcus pyogenes
<220> FEATURE:
<221> NAME/KEY: CDS
<222> LOCATION: (154)..(858)
<223> OTHER INFORMATION:

<400> SEQUENCE: 1
caaccttgac tatttaaatg gaactgccac tcctaaaaac taaaatataa atacatttat      60
aaaatttcta aataaacaga aatctgattt ttaactactt actgctattt catgtattct     120
cgtacgagta atacatttaa ttaaggagaa aaa atg aaa aag att aac atc atc     174
                                     Met Lys Lys Ile Asn Ile Ile
                                     1               5 aaa ata gtt ttc ata att aca gtc ata ctg att tct act tat ttc acc     222
Lys Ile Val Phe Ile Ile Thr Val Ile Leu Ile Ser Thr Tyr Phe Thr
        10                  15                  20 tat cat caa agt gac tct aag aaa gac att tcg aat gtt aaa agt gat     270
Tyr His Gln Ser Asp Ser Lys Lys Asp Ile Ser Asn Val Lys Ser Asp
    25                  30                  35 tta ctt tat gca tac act ata act cct tat gat tat aaa gat tgc agg     318
Leu Leu Tyr Ala Tyr Thr Ile Thr Pro Tyr Asp Tyr Lys Asp Cys Arg
40                  45                  50                  55 gta aat ttt tca acg aca cac aca tta aac att gat act caa aaa tat     366
Val Asn Phe Ser Thr Thr His Thr Leu Asn Ile Asp Thr Gln Lys Tyr
                60                  65                  70 aga ggg aaa gac tat tat att agt tcc gaa atg tct tat gag gcc tct     414
Arg Gly Lys Asp Tyr Tyr Ile Ser Ser Glu Met Ser Tyr Glu Ala Ser
```

-continued

```
                    75                   80                    85
caa aaa ttt aaa cga gat gat cat gta gat gtt ttt gga tta ttt tat    462
Gln Lys Phe Lys Arg Asp Asp His Val Asp Val Phe Gly Leu Phe Tyr
         90                  95                 100 att ctt aat tct cac acc ggt gag tac atc tat gga gga att acg cct    510
Ile Leu Asn Ser His Thr Gly Glu Tyr Ile Tyr Gly Gly Ile Thr Pro
        105                 110                 115 gct caa aat aat aaa gta aat cat aaa tta ttg gga aat cta ttt att    558
Ala Gln Asn Asn Lys Val Asn His Lys Leu Leu Gly Asn Leu Phe Ile
120                 125                 130                 135 tcg gga gaa tct caa cag aac tta aat aac aag att att cta gaa aag    606
Ser Gly Glu Ser Gln Gln Asn Leu Asn Asn Lys Ile Ile Leu Glu Lys
                140                 145                 150 gat atc gta act ttc cag gaa att gac ttt aaa atc aga aaa tac ctt    654
Asp Ile Val Thr Phe Gln Glu Ile Asp Phe Lys Ile Arg Lys Tyr Leu
            155                 160                 165 atg gat aat tat aaa att tat gac gct act tct cct tat gta agc ggc    702
Met Asp Asn Tyr Lys Ile Tyr Asp Ala Thr Ser Pro Tyr Val Ser Gly
        170                 175                 180 aga atc gaa att ggc aca aaa gat ggg aaa cat gag caa ata gac tta    750
Arg Ile Glu Ile Gly Thr Lys Asp Gly Lys His Glu Gln Ile Asp Leu
    185                 190                 195 ttt gac tca cca aat gaa ggg act aga tca gat att ttt gca aaa tat    798
Phe Asp Ser Pro Asn Glu Gly Thr Arg Ser Asp Ile Phe Ala Lys Tyr
200                 205                 210                 215 aaa gat aat aga att atc aat atg aag aac ttt agt cat ttc gat att    846
Lys Asp Asn Arg Ile Ile Asn Met Lys Asn Phe Ser His Phe Asp Ile
                220                 225                 230 tat ctt gaa aaa taattcatca tacacaaaaa accgcccaga ataatctgag         898
Tyr Leu Glu Lys
            235 cggttttgtc ttatctcgga gctttacctc ctaattta                          936
```

<210> SEQ ID NO 2
<211> LENGTH: 235
<212> TYPE: PRT
<213> ORGANISM: Streptococcus pyogenes

<400> SEQUENCE: 2

```
Met Lys Lys Ile Asn Ile Ile Lys Ile Val Phe Ile Ile Thr Val Ile
1               5                   10                  15

Leu Ile Ser Thr Tyr Phe Thr Tyr His Gln Ser Asp Ser Lys Lys Asp
            20                  25                  30

Ile Ser Asn Val Lys Ser Asp Leu Leu Tyr Ala Tyr Thr Ile Thr Pro
        35                  40                  45

Tyr Asp Tyr Lys Asp Cys Arg Val Asn Phe Ser Thr Thr His Thr Leu
    50                  55                  60

Asn Ile Asp Thr Gln Lys Tyr Arg Gly Lys Asp Tyr Tyr Ile Ser Ser
65                  70                  75                  80

Glu Met Ser Tyr Glu Ala Ser Gln Lys Phe Lys Arg Asp Asp His Val
                85                  90                  95

Asp Val Phe Gly Leu Phe Tyr Ile Leu Asn Ser His Thr Gly Glu Tyr
            100                 105                 110

Ile Tyr Gly Gly Ile Thr Pro Ala Gln Asn Asn Lys Val Asn His Lys
        115                 120                 125

Leu Leu Gly Asn Leu Phe Ile Ser Gly Glu Ser Gln Gln Asn Leu Asn
    130                 135                 140
```

-continued

```
Asn Lys Ile Ile Leu Glu Lys Asp Ile Val Thr Phe Gln Glu Ile Asp
145                 150                 155                 160

Phe Lys Ile Arg Lys Tyr Leu Met Asp Asn Tyr Lys Ile Tyr Asp Ala
                165                 170                 175

Thr Ser Pro Tyr Val Ser Gly Arg Ile Glu Ile Gly Thr Lys Asp Gly
            180                 185                 190

Lys His Glu Gln Ile Asp Leu Phe Asp Ser Pro Asn Glu Gly Thr Arg
        195                 200                 205

Ser Asp Ile Phe Ala Lys Tyr Lys Asp Asn Arg Ile Ile Asn Met Lys
    210                 215                 220

Asn Phe Ser His Phe Asp Ile Tyr Leu Glu Lys
225                 230                 235
```

MUTANTS OF STREPTOCOCCAL TOXIN C AND METHODS OF USE

This application is based on International Patent Application PCT/US97/22125 filed Dec. 5, 1997, which is a continuation-in-part of U.S. Provisional Application No. 60/033,251 filed on Dec. 6, 1996.

GOVERNMENT RIGHTS

This invention was made with United States government support under National Institutes of Health #HL36611. The United States government has certain rights in this invention.

BACKGROUND OF THE INVENTION

*Streptococcus pyogenes*, also known as β-hemolytic group A streptococci (GAS) is a pathogen of humans which can cause mild infections such as pharyngitis and impetigo. Post infection autoimmune complications can occur, namely rheumatic fever and acute glomerulonephritis. GAS also causes severe acute diseases such as scarlet fever and streptococcal toxic shock syndrome (STSS). Severe GAS infections were a large problem in the U.S. and throughout the world at the beginning of this century. In the mid-forties, the number of cases and their severity decreased steadily for reasons not yet completely understood. However, more recently, a resurgence of serious diseases caused by GAS has been seen such that there may be 10–20,000 cases of STSS each year in the United States. As many as 50 to 60% of these patients will have necrotizing fascitis and myositis; 30 to 60% will die and as many as one-half of the survivors will have limbs amputated.

In 1986 and 1987 two reports described an outbreak of severe GAS infections localized in the Rocky Mountain area. These reports have been followed in the past few years by several others describing a disease with analogous clinical presentation. The symptoms described for this disease were very similar to those described for toxic shock syndrome (TSS), and in 1992 a committee of scientists gave to this clinical presentation the formal name of STSS, and set the criteria for its diagnosis. STSS is defined by the presence of the following:

1. hypotension and shock;
2. isolation of group A streptococci;
3. two or more of the following symptoms: fever 38.5° C. or higher, scarlet fever rash, vomiting and diarrhea, liver and renal dysfunction, adult respiratory distress syndrome, diffuse intravascular coagulation, necrotizing fascitis and/or myositis, bacteremia.

Streptococcal isolates from STSS patients are predominantly of M type 1 and 3, with M18 and nontypable organisms making up most of the reminder. The majority of M1, 3, 18, and nontypable organisms associated with STSS make pyrogenic exotoxin type A (approx. 75%) with the remainder of the isolates making pyrogenic exotoxin type C (SPE-C). Moreover, administration of SPE-C to a rabbit animal model and in accidental human inoculations can reproduce the symptoms of STSS. In addition to SPE-C association with STSS studies have shown that group A streptococcal isolates from rheumatic fever and guttate psoriasis patients make SPE-C.

SPE-C is a single peptide of molecular weight equal to 24,000 daltons. speC, the gene for SPE-C, has been successfully cloned and expressed in *Escherichia coli*. SPE-C is a member of a large family of exotoxins produced by streptococci and staphylococci, referred to as pyrogenic toxins based upon their ability to induce fever and enhance host susceptibility up to 100,000 fold to endotoxin.

Recently these toxins have been referred to as superantigens because of their ability to induce massive proliferation of T lymphocytes, regardless of their antigenic specificity, and in a fashion dependent on the composition of the variable part of the β chain of the T cell receptor. These toxins also stimulate massive release of IFN-γ, IL-1, TNF-α and TNF-β. Other members of this family are streptococcal pyrogenic exotoxins type A and B, staphylococcal toxic shock syndrome toxin 1, staphylococcal enterotoxins A, B, Cn, D, E, G and H, and non-group A streptococcal pyrogenic exotoxins. These toxins have similar biochemical properties, biological activities and various degrees of sequence similarity.

The most severe manifestations of STSS are hypotension and shock, that lead to death. It is generally believed that leakage of fluid from the intravascular to the interstitial space is the final cause of hypotension, supported by the observation that fluid replacement therapy is successful in preventing shock in the rabbit model of STSS described above. It has been hypothesized that SPE-C may act in several ways on the host to induce this pathology.

SPE-C has been shown to block liver clearance of endotoxin of endogenous flora's origin, by compromising the activity of liver Kuppfer cells. This appears to cause a significant increase in circulating endotoxin, that through binding to lipopolysaccharide binding protein (LBP) and CD14 signaling leads to macrophage activation with subsequent release of TNF-α and other cytokines. Support for the role of endotoxin in the disease is given by the finding that the lethal effects of SPE-C can be at least partially neutralized by the administration to animals of polymyxin B or by the use of pathogen free rabbits.

Another modality of induction of shock could be the direct activity of the toxin on capillary endothelial cells. This hypothesis stems from the finding that the staphylococcal pyrogenic toxin TSST-1 binds directly to human umbilical cord vein cells and is cytotoxic to isolated porcine aortic endothelial cells.

Another of the toxin's modality of action includes its superantigenicity, in which the toxin interacts with and activates up to 50% of the host T lymphocytes. This massive T cell stimulation results in an abnormally high level of circulating cytokines TNF-β and IFN-γ which have direct effects on macrophages to induce release of TNF-α and IL-1. These cytokines may also be induced directly from macrophages by SPE-C through MHC class II binding and signaling in the absence of T cells. The elevated levels of TNF-α and -β cause several effects typically found in Gram negative induced shock, among which is damage to endothelial cells and capillary leak. However, the administration to SPE-A treated rabbits of cyclosporin A, which blocks upregulation of IL-2 and T cell proliferation, did not protect the animals from shock, suggesting that additional mechanisms may be more important in causing capillary leak.

Thus, there is a need to localize sites on the SPE-C molecule responsible for different biological activities. There is a need to develop variants of SPE-C that have changes in biological activities such as toxicity and mitogenicity. There is a need to develop compositions useful in vaccines to prevent or ameliorate streptococcal toxic shock syndrome. There is also a need to develop therapeutic agents useful in the treatment of streptococcal toxic shock syndrome and other diseases.

SUMMARY OF THE INVENTION

This invention includes mutant SPE-C toxins and fragments thereof, vaccines and pharmaceutical compositions and methods of using vaccines and pharmaceutical compositions.

Mutant SPE-C toxins have at least one amino acid change and are substantially nonlethal as compared with a protein substantially corresponding to a wild type SPE-C toxin. For vaccine compositions, mutant toxins also stimulate a protective immune response to at least one biological activity of a wild type SPE-C toxin. Mutant toxins for vaccine compositions are optionally further selected to have a decrease in enhancement of endotoxin shock and a decrease in T cell mitogenicity when compared to the wild type SPE-C. For pharmaceutical compositions, it is preferred that a mutant toxin is substantially nonlethal while maintaining T cell mitogenicity comparable to a wild type SPE-C toxin.

The invention also includes fragments of a wild type SPE-C toxin and mutants of SPE-C toxins. Fragments and peptides derived from wild type SPE-C are mutant SPE-C toxins. Fragments can include different domains or regions of the molecule joined together. A fragment is substantially nonlethal when compared to a wild type SPE-C toxin. For mutant toxins, a fragment has at least one amino acid change compared to a wild type SPE-C amino acid sequence. Fragments are also useful in vaccine and pharmaceutical compositions.

The invention also includes expression cassettes, vectors and transformed cells. An expression cassette comprises a DNA sequence encoding a mutant SPE-C toxin or fragment thereof operably linked to a promoter functional in a host cell. DNA cassettes are preferably inserted into a vector. Vectors include plasmids or viruses. Vectors are useful to provide template DNA to generate DNA encoding a mutant SPE-C toxin. DNA cassettes and vectors are also useful in vaccine compositions. Nucleic acids encoding a mutant SPE-C toxin or fragment thereof can be delivered directly for expression in mammalian cells. The promoter is preferably a promoter functional in a mammalian cell. Nucleic acids delivered directly to cells can provide for expression of the mutant SPE-C toxin in an individual so that a protective immune response can be generated to at least one biological activity of a wild type SPE-C toxin.

Additional vaccine compositions include stably transformed cells or viral vectors including an expression cassette encoding a mutant SPE-C toxin or fragment thereof. Viral vectors such as vaccinia can be used to immunize humans to generate a protective immune response against at least one biological activity of a wild type SPE-C toxin. Transformed cells are preferably microorganisms such as *S. aureus*, *E. coli*, or *Salmonella* species spp. Transformed microorganisms either include mutant SPE-C toxin or fragment thereof on their surface or are capable of secreting the mutant toxin. Transformed microorganisms can be administered as live, attenuated or heat killed vaccines.

The invention also includes methods of using vaccines and pharmaceutical compositions. Vaccines are administered to an animal in an amount effective to generate a protective immune response to at least one biological activity of a wild type SPE-C toxin. Preferably, the vaccine compositions are administered to humans and protect against the development of STSS. Pharmaceutical compositions are used in methods of stimulating T cell proliferation.

The mutant SPE-C toxins and/or fragments thereof and other vaccine compositions can be useful to generate a passive immune serum. Mutant SPE-C toxins or fragments thereof, DNA expression cassettes or vectors, or transformed microorganisms can be used to immunize an animal to produce neutralizing antibodies to at least one biological activity of wild type SPE-C. The neutralizing antibodies immunoreact with a mutant SPE-C toxin and/or fragment thereof and the wild type SPE-C toxin. Passive immune serum can be administered to an animal with symptoms of A streptococcal infection and STSS.

BRIEF DESCRIPTION OF THE FIGURES

FIG. 1 shows the nucleotide sequence of speC (SEQ ID NO: 1). Numbering is in reference to the ATG start codon. Possible promoter (−10, −35) and Shine-Dalgarno (SD) sequences are noted. The deduced amino acid sequence (SEQ ID NO: 2) is given below the nucleotide sequence (SEQ ID NO: 1). An asterisk after residue 27 indicates the cleavage site between the signal peptide and mature protein. Overlined nucleotides 3' of the translation stop codon are palindromic sequences.

DETAILED DESCRIPTION OF THE INVENTION

Figure 2:
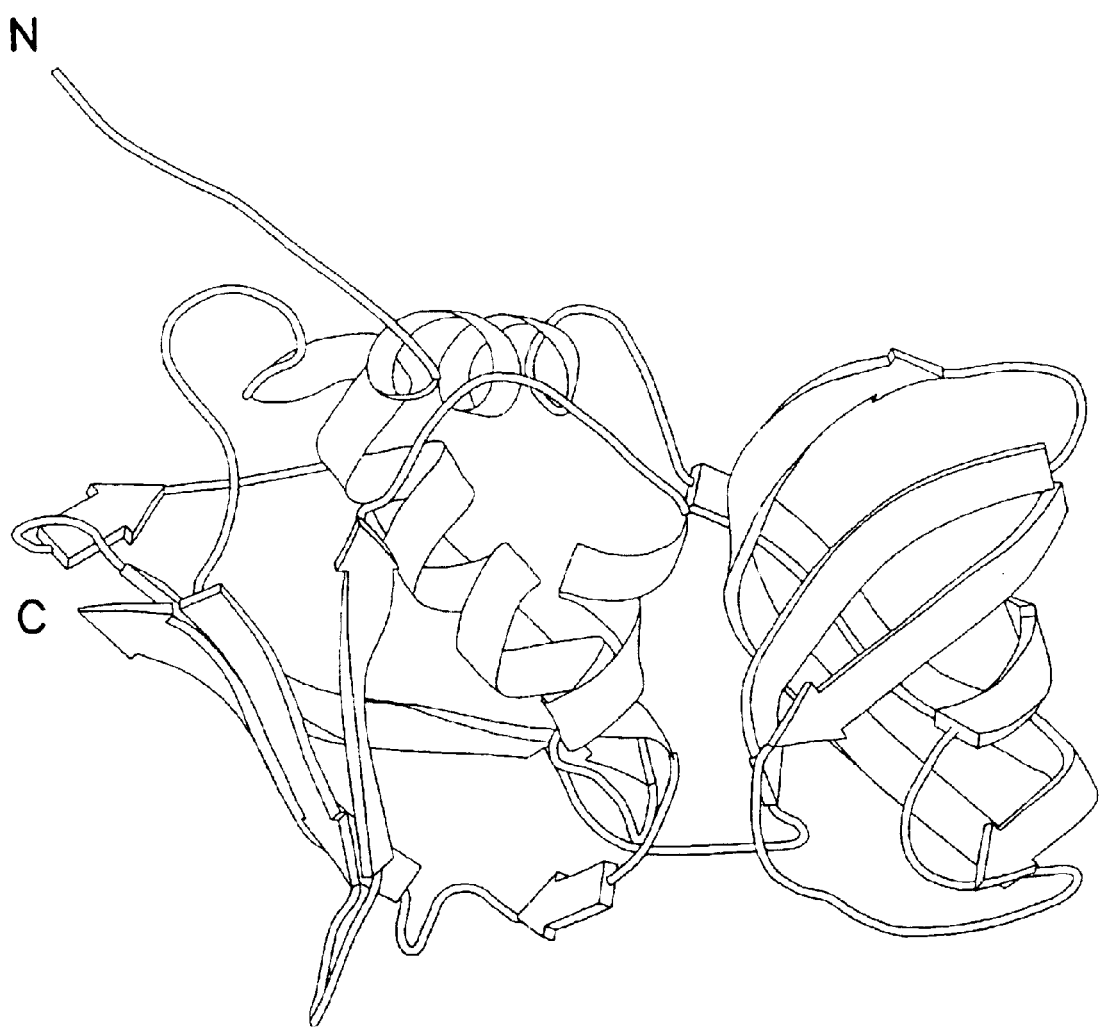
FIG. 2 shows a front view of a ribbon structure of SPE-C.

This invention is directed to mutant SPE-C toxins and fragments thereof, vaccine and pharmaceutical compositions including mutant SPE-C toxins or fragments thereof, methods of preparing mutant SPE-C toxins and fragments thereof, and methods of using SPE-C toxins and fragments thereof.

Mutant SPE-C toxins are proteins that have at least one amino acid change and have at least one change in a biological function compared with a protein substantially corresponding to a wild type SPE-C toxin. Preferably, the mutant SPE-C toxin is substantially nonlethal when compared to a wild type SPE-C toxin at the same dose. Mutant SPE-C toxins can be generated using a variety of methods including site-directed mutagenesis, random mutagenesis, conventional mutagenesis, in vitro mutagenesis, spontaneous mutagenesis and chemical synthesis. Mutant SPE-C toxins are preferably selected to: 1) ensure at least one change in an amino acid; and 2) to have a change in at least one biological function of the molecule preferably a decrease or elimination of systemic lethality. The mutant toxins are useful in vaccine compositions for protection against at least one biological activity of SPE-C toxin such as prevention or amelioration of STSS and in methods of treating animals with symptoms of STSS.

A. Mutant SPE-C Toxins or Fragments Thereof, Vaccine and Pharmaceutical Compositions The invention includes mutant SPE-C toxins that have at least one amino acid change and that have at least one change in a biological activity compared with proteins that substantially correspond to and have the same biological activities as wild type SPE-C.

Wild type SPE-C toxin is encoded by a gene speC. The wild type SPE-C toxin has a molecular weight of 24,000 Daltons as determined by SDS PAGE of purified protein. A DNA sequence encoding a wild type SPE-C toxin and the predicted amino acid sequence for a wild type SPE-C toxin is shown in FIG. 1. A DNA sequence encoding a wild type SPE-A toxin has been cloned in E. coli and S. aureus. Amino acid number designations in this application are made by reference to the sequence of FIG. 1 with aspartate at position 28 designated as the first amino acid. The first 27 amino acids represent a leader sequence not present in the mature protein.

The wild type SPE-C toxin has several biological activities. These biological activities include: 1) fever; 2) STSS; 3) systemic lethality due to development of STSS or enhancement of endotoxin shock; 4) enhancing endotoxin shock; 5) induction of capillary leak and hypotension; 6) inducing release of cytokines such as IFN γ, IL-1, TNF-α and TNF-β; 7) binding to porcine aortic endothelial cells; 8) binding to MHC class II molecules; 9) binding to T-cell receptors; and 10) T-cell mitogenicity (superantigenicity). These activities can be assayed and characterized by methods known to those of skill in the art.

As used herein, the definition of a wild type SPE-C toxin includes variants, such as allelic variants, of a wild type SPE-C toxin that have the same biological activity of wild type SPE-C toxin. These SPE-C toxins may have a different amino acid or their genes may have a different nucleotide sequence from that shown in FIG. 1 but do not have different biological activities. Changes in amino acid sequence are phenotypically silent. Preferably, these toxin molecules have systemic lethality and enhance endotoxin shock to the same degree as wild type SPE-C toxin shown in FIG. 1. Preferably these toxins have at least 60–99% homology with wild type SPE-C toxin amino acid sequence as shown in FIG. 1 as determined using the SS2 Alignment Algorithm as described by Altschul, S. F., Bull. Math. Bio. 48:603 (1986). Proteins that have these characteristics substantially correspond to a wild type SPE C.

A mutant SPE-C toxin is a toxin that has at least one change in a amino acid compared with a protein substantially corresponding to a wild type SPE-C toxin. The change can be an amino acid substitution, deletion, or addition. There can be more than one change in the amino acid sequence, preferably 1 to 6 changes. It is preferred that there is more than one change in the amino acid sequence to minimize the reversion of mutant SPE-C toxin to the wild type SPE-C toxin having systemic lethality or toxicity. For mutant SPE-C toxins useful in vaccines, it is preferred that the change in the amino acid sequence of the toxin does not result in a change of the toxin's ability to stimulate an antibody response that can neutralize wild type SPE-C toxin. For mutant SPE-C toxins useful in vaccines, it is especially preferred that the mutant toxins are recognized by polyclonal neutralizing antibodies to SPE-C toxin such as from Toxin Technologies in Boca Raton, Fla. or Dr. Schlievert (University of Minnesota, Minneapolis, Minn.) and that the proteolytic profile is not altered compared with wild type SPE-C.

The changes in the amino acid sequence can be site-specific changes at one or more selected amino acid residues of a wild type SPE-C toxin. Site-specific changes are selected by identifying residues in particular domains of the molecule as described or at locations where cysteine residues are located. Site-specific changes at a particular location can optionally be further selected by determining whether an amino acid at a location or within a domain is identical to or has similar properties to an equivalent residue in other homologous molecules by comparison of primary sequence homology or 3-D conformation. A homologous molecule is one that can be identified by comparison of primary sequence homology using the SS2 alignment algorithm of Altschul et al., cited supra or a homology modeling program such as Insight/Homology from BioSym, San Diego, Calif. A homologous molecule is one that displays a significant number, typically 30–99%, of identical or conservatively changed amino acids or has a similar three dimensional structure, typically RMS error for conserved regions of <2 Angstroms, when compared to a wild type SPE-C toxin.

Changes in the amino acid sequence at a particular site can be randomly made or specific changes can be selected. Once a specific site is selected it is referred to by its amino acid number designation and by the amino acid found at that site in the wild type SPE-C as shown in FIG. 1. The amino acid number designations made in this application are by reference to the sequence in FIG. 1 with the aspartate at position 28 being counted as the first amino acid. Equivalent amino acids corresponding to those identified at a particular site in proteins substantially corresponding to a wild type SPE-C toxin may have different amino acid numbers depending on the reference sequence or if they are fragments. Equivalent residues are also those found in homologous molecules that can be identified as equivalent to amino acids in proteins substantially corresponding to a wild type SPE-C toxin either by comparison of primary amino acid structure or by comparison to a modeled structure as shown in FIG. 1 or by comparison to a known crystal structure of a homologous molecule. It is intended that the invention cover changes to equivalent amino acids at the same or similar locations regardless of their amino acid number designation.

If a specific substitution is selected for an amino acid at a specific site, the amino acid to be substituted at that location is selected to include a structural change that can affect biological activity compared with the amino acid at that location in the wild type SPE-C. The substitution may be conservative or nonconservative. Substitutions that result in a structural change that can affect biological activity include: 1) change from one type of charge to another; 2) change from charge to noncharged; 3) change in cysteine residues and formation of disulfide bonds; 4) change from hydrophobic to hydrophilic residues or hydrophilic to hydrophobic residues; 5) change in size of the amino acids; 6) change to a conformationally restrictive amino acid or analog; and 7) change to a non-naturally occurring amino acid or analog. The specific substitution selected may also depend on the location of the site selected. For example, it is preferred that amino acids in the N-terminal alpha helix have hydroxyl groups to interact with exposed amide nitrogens or that they be negatively charged to interact with the partial positive charge present at the N-terminus of the α helix.

Mutant toxins may also include random mutations targeted to a specific site or sites. Once a site is selected, mutants can be generated having each of the other 19 amino acids substituted at that site using methods such as described by Aiyar et al., Biotechniques 14:366 (1993) or Ho et al. Gene 77:51–54 (1984). In vitro mutagenesis can also be utilized to substitute each one of the other 19 amino acids or non-naturally occurring amino acids or analogs at a particular location using a method such as described by Anthony-Cahill et al., Trends Biochem. Sci. 14:400 (1989).

Mutant toxins also include toxins that have changes at one or more sites of the molecule not specifically selected and that have a change in amino acids that is also not specifically selected but can be any one of the other 19 amino acids or a non-naturally occurring amino acid.

Substitutions at a specific site can also include but are not limited to substitutions with non-naturally occurring amino acids such as 3-hydroxyproline, 4-hydroxyproline, homocysteine, 2-aminoadipic acid, 2-aminopimilic acid, ornithine, homoarginine, N-methyllysine, dimethyl lysine, trimethyl lysine, 2,3-diaminopropionic acid, 2,4-diaminobutryic acid, hydroxylysine, substituted phenylalanine, norleucine, norvaline, (-valine and halogenated tyrosines. Substitutions at a specific site can also include the use of analogs which use non-peptide chemistry including but not limited to ester, ether and phosphoryl and boron linkages.

The mutant toxins can be generated using a variety of methods. Those methods include site-specific mutagenesis, mutagenesis methods using chemicals such as EMS, or sodium bisulfite or UV irradiation, by spontaneous mutation, by in vitro mutagenesis and chemical synthesis. Methods of mutagenesis can be found in Sambrook et al., A Guide to Molecular Cloning, Cold Spring Harvard, N.Y. (1989). The especially preferred method for site-specific mutagenesis is using asymmetric PCR with three primers as described by Perrin and Gilliland, 1990. Nucleic Acid Res. 18:7433.

Superpositioning the three-dimensional structures of four staphylococcal superantigens (TSST-1, SEA, SEB, and SEC-3) and of SPE-C demonstrated that these proteins share 16 structurally conserved amino acids (Table 1). Using these 16 structurally conserved amino acid residues as reference points allows superpositioning of the structures of these 5 proteins with RMS (root mean square) differences at or below 2 angstroms, which is significant for proteins with minimal amino acid sequence conservation. This superpositioning based on 16 structurally conserved amino acids allows detailed comparison of the structure of SPE-C with the staphylococcal superantigens.

The crystal structure of the complex of staphylococcal superantigen SEB and the class II major histocompatibility complex (MHC-II) shows amino acids on SEB that contact MHC-II, and includes those residues listed in Table 2. Superposition of the SPE-C structure indicates the location of portions of SPE-C that contact MHC-II in a complex of these two proteins. These locations are shown in FIG. 4 as balls.

Figure 4:
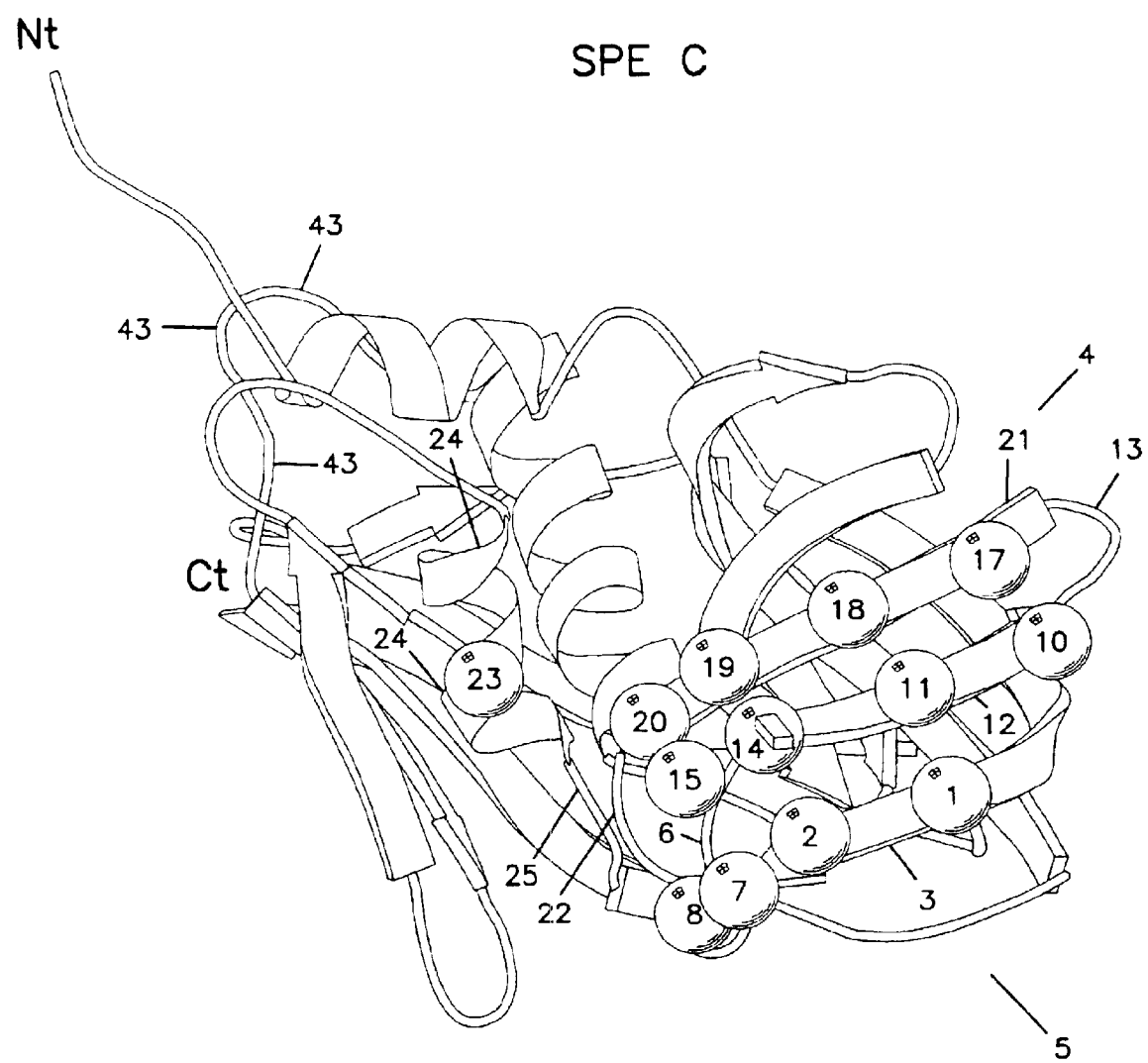
FIG. 4 shows a front view of a ribbon structure of SPE-C oriented to show locations contacting major histocompatibility complex type II in a complex.

Specifically, with reference to FIG. 4, these include locations 1 and 2 on strand 3 of β-barrel 4 of B-subunit 5. Location 1 is the position of an amino acid 1 residue past a type 4 turn or bulge in strand 3 and about three residues from the junction of strand 3 and loop 6. Location 1 can be occupied by a polar amino acid preferably Thr-33 of SPE-C. Location 2 represents the amino acid in strand 3 closest to the junction of strand 3 and loop 6, while remaining on the strand. Location 2 can be occupied by a polar amino acid, preferably His-35 of SPE-C. Location 7 represents the amino acid nearest the junction of strand 3 and loop 6. Loop 6 is a "type 1" or "type 2" turn. Location 7 can be a hydrophobic amino acid, preferably Leu-37 of SPE-C. β-Barrel 4 of B-subunit 5 also includes residue Asn-38.

Location 8 is in loop 6. Location 8 can be occupied by a polar amino acid, preferably Asn-38 of SPE-C. Locations 10, 11 and 14 are on strand 12. Location 10 is the amino acid on strand 12 nearest the junction with loop 13. Location 10 can be a charged amino acid, preferably Arg-45 of SPE-C. Location 11 is at about the middle of strand 12 and can be occupied by a charged amino acid, preferably Lys-43 of SPE-C. Location 14 is at the junction of strand 12 and loop 6 but on strand 12. Location 14 can be occupied by a polar amino acid, preferably Thr-41 of SPE-C. Location 15 is on loop 6. Location 15 can be occupied by a charged amino acid, preferably Asp-40 of SPE-C.

Locations 17–20 are on strand 21. Locations 19 and 20 are adjacent. Locations 17–19 are separated with room enough for a location between each. Location 17 is about one amino acid from the junction of strand 21 and loop 13. Location 17 can be occupied by a hydrophobic amino acid, preferably Ile-51 of SPE-C. Location 18 is at approximately the midpoint of strand 21 and can be occupied by a neutral or polar amino acid, preferably amino acid Ser-52 of SPE-C. Location 19 is about two amino acids from the junction of strand 21 and loop 22. Location 19 can be occupied by a neutral or polar amino acid, preferably Met-55 of SPE-C. Location 20 is in strand 21 adjacent to the junction of strand 21 with loop 22. Location 20 can be occupied by a neutral or polar amino acid, preferably Ser-56 of SPE-C. Location 23 is on alpha helix 24 in the turn and ending with the junction of helix 24 and loop 25. Location 23 is on a face of helix 24 facing location 20. Location 23 can be occupied by a neutral amino acid, preferably Ala-186 of SPE-C.

The crystal structure of the complex of staphylococcal superantigen SEC-3 and the T cell receptor shows amino acids on SEC-3 that contact T cell receptor, and includes residues listed in Table 3. Superposition of the SPE-C structure indicates the location of amino acids of SPE-C that contact the T cell receptor in a complex of these two proteins. These locations are shown in FIG. 5 as balls.

Figure 5:
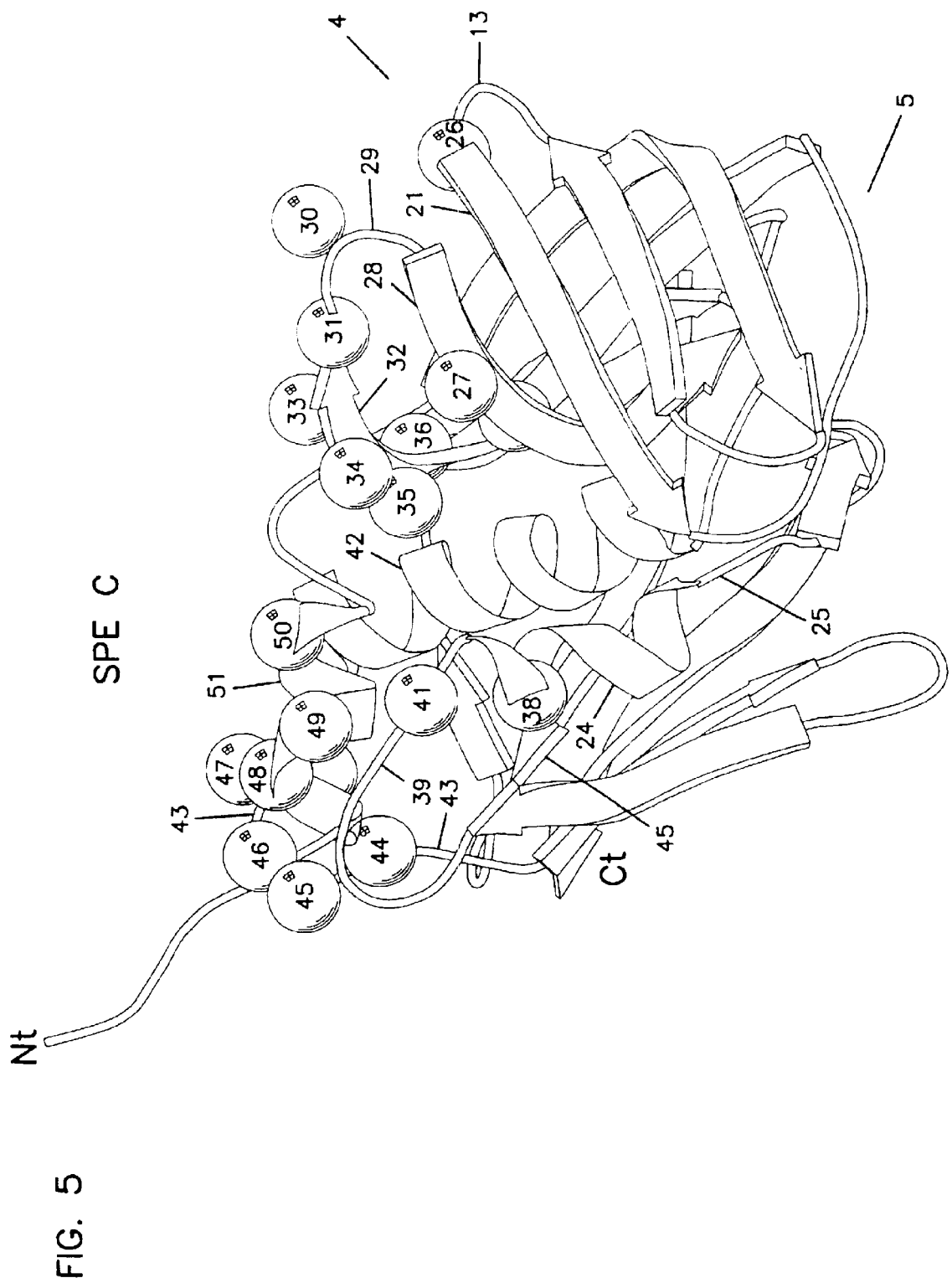
FIG. 5 shows a front view of a ribbon diagram of SPE-C oriented to show locations that contact the T cell receptor in a complex.
Figure 6:
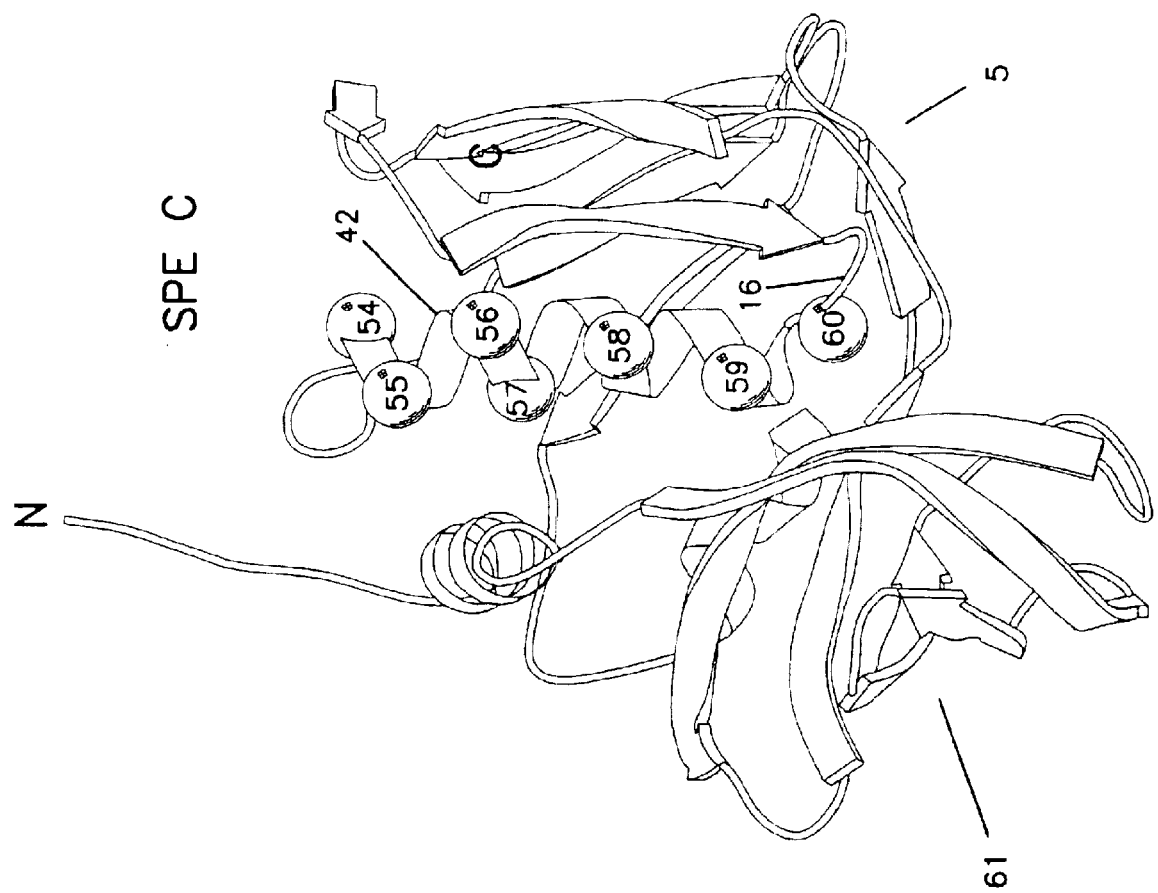
FIG. 6 shows a rear view of a ribbon structure of SPE-C oriented to show residues of the central α helix that form the floor of the groove that contacts the liver renal tubular cell receptor in a complex with this receptor.

Specifically, with reference to FIG. 5, these include location 26 which is at the junction of loop 13 and strand 21. Location 26 can be occupied by a polar amino acid, preferably Tyr-49 of SPE-C. Location 27 is on strand 28 approximately the distance of three amino acids from the junction of strand 28 with loop 29. Location 27 can be occupied by a polar amino acid, preferably Tyr-85 of SPE-C. Location 30 is on loop 29 approximately equidistant between strands 28 and 32. Location 30 can be occupied by a polar amino acid, preferably His-81 of SPE-C. Location 31 is at the junction of loop 29 and strand 32. Location 31 can be occupied by a polar amino acid, preferably Asn-79 of SPE-C. Locations 33–36 are on strand 32. Location 33 is the amino acid adjacent to the junction of strand 32 and loop 31. Position 33 can be occupied by hydrophobic amino acid, preferably Leu-78 of SPE-C. Location 34 is one amino acid from location 33. Location 34 can be occupied by a hydrophobic amino acid, preferably Ile-77 of SPE-C. Location 35 can be occupied by a polar amino acid, preferably Tyr-76 of SPE-C. Location 36 can be occupied by a hydrophobic amino acid, preferably Phe-75 of SPE-C.

Location 38 is a residue on irregular alpha helix 24 on a turn of that alpha helix nearest the junction with loop 39. Location 38 is on a portion of the turn nearest strand 40. Location 38 can be occupied by a charged amino acid, preferably Asp-183 of SPE-C. Location 41 is on loop 39 approximately one amino acid from the junction of loop 39 and alpha helix 24. A side chain on an amino acid at location 41 is oriented toward central alpha helix 42. Location 41 can be occupied by a charged amino acid, preferably Arg-181 of SPE-C.

Loop 43 includes locations 44, 45, 46, and 47. Locations 44–47 are adjacent locations on the portion of loop 43 most exposed to the solvent. Location 44 can be occupied by a charged amino acid, preferably Glu-178 of SPE-C. Location 45 can be occupied by a polar amino acid, preferably Tyr-153 of SPE-C. Location 46 can be occupied by a charged amino acid, preferably Asp-148 of SPE-C. Location 47 can be occupied by a polar amino acid, preferably Tyr-147 of SPE-C.

Locations 48–50 are on N-terminal alpha helix 51. Locations 48 and 49 are on a turn of alpha helix 51 nearest the junction with loop 52. Location 48 can be occupied by a neutral or polar amino acid, preferably Ser-11 of SPE-C. Location 49 can be occupied by a charged amino acid, preferably Asp-12 of SPE-C. Locations 48 and 49 represent adjacent amino acid positions. Location 50 is in the turn of alpha helix 51 adjacent to the junction with loop 53. Location 50 is on the portion of that turn that is most solvent-exposed. Location 50 can be occupied by a polar amino acid, preferably Tyr-15 of SPE-C. N-terminal alpha helix 51 also includes residue Tyr-17.

SPE-C binds a liver renal tubular cell receptor at a site including residues on a groove on the "back" of SPE-C. Locations 54–60 define a surface of a groove on SPE-C between B subunit 5 and A subunit 61 that is part of the interaction with the liver renal tubular cell receptor. Locations 54–59 are on central alpha helix 42. Location 60 is on loop 16 adjacent to the junction of loop 16 with central alpha helix 42. Location 54 can be occupied by a polar amino acid, preferably Asn-143 of SPE-C. Location 55 can be occupied by a charged amino acid, preferably Asp-142 of SPE-C. Location 56 can be occupied by a polar amino acid, preferably Tyr-139 of SPE-C. Location 57 can be occupied by a charged amino acid, preferably Lys-138 of SPE-C. Location 58 can be occupied by a positively charged amino acid, preferably Lys-135 of SPE-C. Location 59 can be occupied by a charged amino acid, preferably Glu-131 of SPE-C. Location 60 can be occupied by a neutral or polar amino acid, preferably Thr-128 of SPE-C.

Table 2 lists residues of SEB that interact with class II MHC in the crystal structure of the complex of these two proteins. Superposition of the structures of SEC-3, SEA and TSST-1 with the structure of the SEB:MHC-II complex indicates amino acids on these proteins that correspond to the listed SEB residues that interact with MHC-II. Preferred SPE-C mutants have an amino acid substitution at an SPE-C residue that corresponds to a residue in SEB, SEC-3, SEA or TSST-1 that interacts with MHC-II. These preferred SPE-C residues include the SPE-C residues listed in Table 2. Corresponding residues from the different proteins are listed across the rows of the table.

Table 3 lists residues of SEC-3 that interact with the T-cell receptor in the crystal structure of the complex of these two proteins. Superposition of the structures of SEB, SEA and TSST-1 with the structure of the SEC-3:T-cell receptor complex indicates amino acids on these proteins that correspond to the SEC residues that interact with T-cell receptor. Preferred SPE-C mutants have an amino acid substitution at an SPE-C residue that corresponds to a residue in SEB, SEC-3, SEA or TSST-1 that interacts with the T-cell receptor. These preferred SPE-C residues include the SPE-C residues listed in Table 3. Corresponding residues from the different proteins are listed across the rows of the table.

Preferred mutants of SPE-C have amino acid substitutions in at least one of the locations or for at least one of the amino acid residues that interacts with the T-cell receptor, MHC-II or the liver renal tubular cell receptor. These amino acid substitutions can be chosen as described hereinabove to disrupt the interactions.

TABLE 1

PTSAG CONSERVED RESIDUES

| TSST-1 | SEA | SEB | SEC-3 | SPE-C |
|---|---|---|---|---|
| TYR 13 | TYR 30 | TYR 28 | TYR 28 | TYR 17 |
| ASP 27 | ASP 45 | ASP 42 | ASP 42 | (THR 33) |
| LYS 58 | LYS 81 | LYS 78 | LYS 78 | (ARG 65) |
| VAL 62 | VAL 85 | VAL 82 | VAL 82 | VAL 69 |
| ASP 63 | ASP 86 | ASP 83 | ASP 83 | ASP 70 |
| GLY 87 | GLY 110 | GLY 117 | GLY 114 | GLY 89 |
| THR 89 | THR 112 | THR 119 | THR 116 | THR 91 |
| LYS 121 | LYS 147 | LYS 152 | LYS 151 | LYS 124 |
| LYS 122 | LYS 148 | LYS 153 | LYS 152 | (ASP 125) |
| LEU 129 | LEU 155 | LEU 160 | LEU 159 | (ILE 132) |
| ASP 130 | A5P 156 | ASP 161 | ASP 160 | ASP 133 |
| ARG 134 | ARG 160 | ARG 162 | ARG 161 | ARG 137 |
| LEU 137 | LEU 163 | LEU 168 | LEU 167 | LEU 140 |
| LEU 143 | LEU 169 | LEU 171 | LEU 170 | (ILE 146) |
| TYR 144 | TYR 170 | TYR 172 | TYR 171 | TYR 147 |
| GLY 152 | GLY 182 | GLY 185 | GLY 184 | GLY 156 |
| ASP 167 | ASP 197 | ASP 199 | ASP 199 | ASP 171 |
| ILE 189 | ILE 226 | ILE 230 | ILE 230 | ILE 204 |

TABLE 2

RESIDUES INVOLVED IN CLASS II MHC INTERACTIONS

| SEB | TSST-1 | SEA | SEC-3 | SPE-C |
|---|---|---|---|---|
| Gln 43 | Asn 28 | Gln 46 | Lys 43 | His 35 |
| Phe 44 | Ser 29 | Phe 47 | Phe 44 | His 35 |
| Leu 45 | | Leu 48 | Leu 45 | Leu 37 |
| Tyr 46 | Leu 30 | Gln 49 | Ala 46 | Asn 38 |
| Phe 47 | Gly 31 | His 50 | His 47 | |
| Gln 92 | Lys 71 | Gln 95 | Asn 92 | Leu 78 |
| Tyr 94 | Gln 73 | Ala 97 | Tyr 94 | Ser 80 |
| Ser 96 | | Gly 99 | Ser 96 | |
| Met 215 | Asn 175 | Arg 211 | Met 215 | Ala 186 |

TABLE 3

RESIDUES INVOLVED IN TCR INTERACTIONS

| TSST-1 | SEC-3 | SEA | SEB | SPE-C |
|---|---|---|---|---|
| ASN 5 | GLY 19 | THR 21 | GLY 19 | ASN 8 |
| | THR 20 | ALA 22 | LEV 20 | SER 11 |
| ASP 8 | ASN 23 | ASN 25 | ASN 23 | ASP 12 |
| ASP 11 | TYR 26 | GLN 28 | VAL 26 | TYR 15 |
| | ASN 60 | | | TYR 49 |
| LYS 70 | TYR 90 | GLY 93 | TYR 90 | ILE 77 |
| | VAL 91 | TYR 94 | TYR 91 | LEU 78 |
| | GLY 102 | | | ASN 79 |
| | LYS 103 | | | |
| | VAL 104 | | | |
| | SER 106 | LYS 103 | | |
| ARG 145 | PHE 176 | ASN 171 | TYR 175 | ASP 148 |
| | GLN 210 | SER 206 | GLN 210 | ARG 181 |

Once a mutant SPE-C toxin is generated having at least one amino acid change compared with a protein substantially corresponding to the wild type SPE-C toxin, the mutant SPE-C toxin is screened for nonlethality. It is preferred that mutant SPE-C toxins selected from this screening are substantially nonlethal in rabbits when administered using a miniosmotic pump (as described in Example 4) at the same dose or a greater dose than a wild type SPE-C toxin. A mutant SPE-C toxin or fragment thereof is substantially nonlethal if when administered to a rabbit at the same dose as the wild type toxin less than about 10–20% of rabbits die.

Nonlethal mutant toxins are useful in vaccine and pharmaceutical compositions. While not meant to limit the invention, it is believed that some amino acid residues or domains that affect systemic lethality are separable from other biological activities especially T cell mitogenicity.

For mutant toxins useful in vaccine compositions it is further preferred that the mutant SPE-C toxins are screened for those that can stimulate an antibody response that neutralizes wild type SPE-C toxin activity. A method for selecting mutant toxins that can stimulate an antibody response that neutralizes wild type SPE-C toxin activity is to determine whether the mutant toxin immunoreacts with polyclonal neutralizing antibodies to wild type SPE-C such as available from Toxin Technologies, Boca Raton, Fla. or Dr. Schlievert. Methods of determining whether mutant SPE-C toxins immunoreact with antibodies to wild type SPE-C toxin include ELISA, Western Blot, Double Immunodiffusion Assay and the like.

Figure 3:
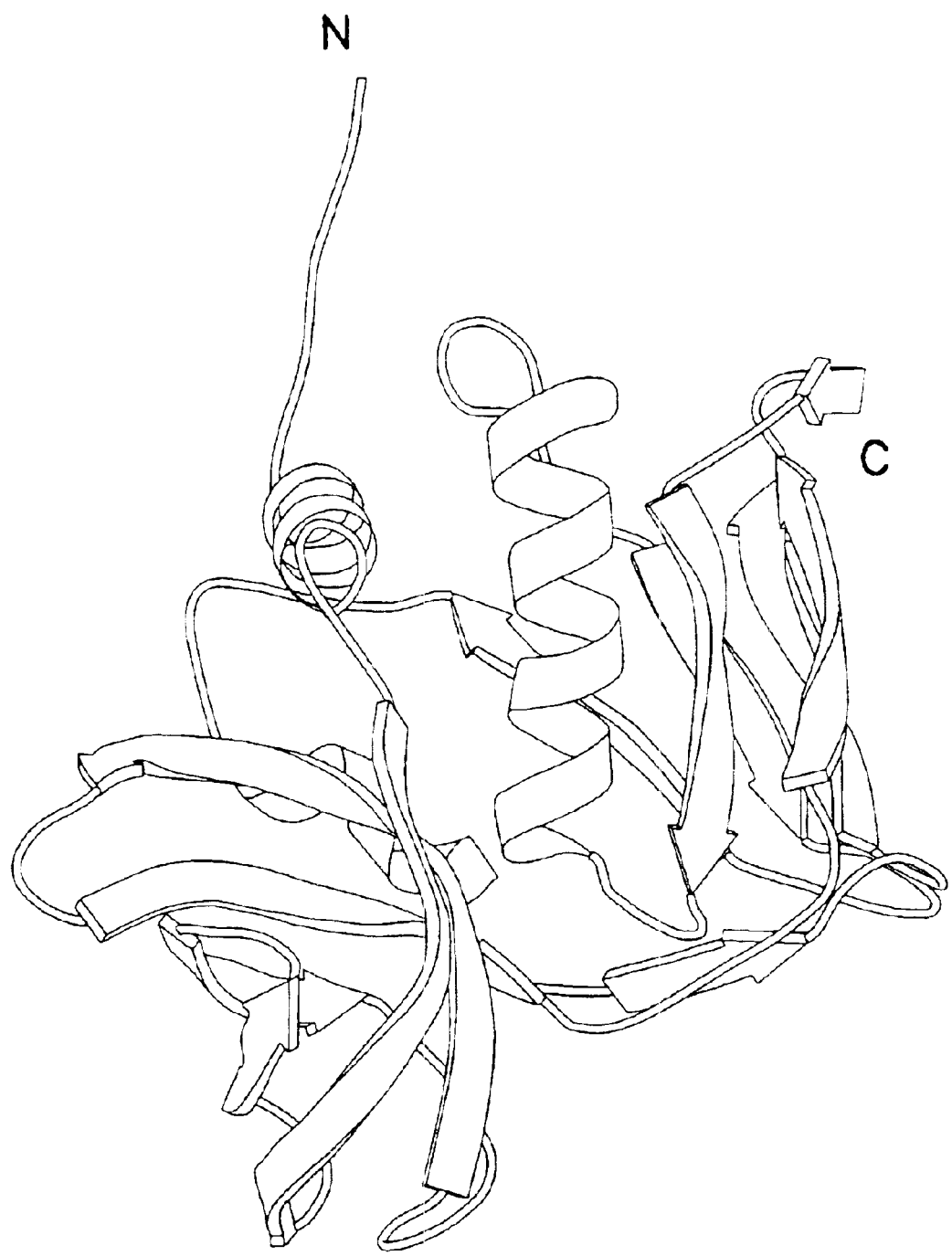
FIG. 3 shows a back view of a ribbon structure of SPE-C.

Optionally, the mutant toxins can also be screened to determine if the proteolytic profile of the mutant toxin is the same as the wild type SPE-C toxin. In some cases, it is preferred that the mutants generated do not substantially change the overall three-dimensional conformation of the mutant toxin compared with the wild type SPE-C toxin. One way of examining whether there has been a change in overall conformation is to look at immunoreactivity of antibodies to wild type SPE-C toxin and/or to examine the proteolytic profile of mutant SPE-C toxins. The proteolytic profile can be determined using such enzymes as trypsin, chymotrypsin, papain, pepsin, subtilisin and V8 protease in methods known to those of skill in the art. The proteolytic profile of wild type SPE-C with the sequence shown in FIG. 3 is known. The mutants that have a similar profile to that of wild type SPE-C are selected.

Optionally, mutant toxins can also be screened and selected to have other changes in biological activity. As described previously, there are several biological activities associated with wild type SPE-C toxin. Those biological activities include: 1) fever; 2) STSS; 4) enhancement of endotoxin shock; 5) capillary leak and hypotension; 6) inducing release of cytokines such as IFN gamma, IL-1, TNF-α and TNF-β; 7) binding to endothelial cells; 8) binding to MHC class II molecules; 9) binding to T-cell receptors; and 10) T-cell mitogenicity (superantigenicity). These biological activities can be measured using methods known to those of skill in the art.

For mutant SPE-C toxins or fragments thereof useful in vaccine compositions, it is preferred that they are substantially nontoxic and immunoreactive with neutralizing antibodies to wild type SPE-C. Neutralizing antibodies include those that inhibit the lethality of the wild type toxin when tested in animals. Optionally, mutant SPE-C toxins can have a change in one or more other biological activities of wild type SPE-C toxin as described previously.

Optionally, preferred mutant toxins for vaccine compositions are further screened and selected for a lack of potentiation of endotoxin shock. The preferred assay for examining a lack of enhancement of endotoxin shock is described in Example 3. Rabbits preferably have no demonstrable bacterial or viral infection before testing. A lack of potentiation of or substantially no enhancement of endotoxin shock is seen when less than about 25% of the animals develop shock when the mutant SPE-C toxin is coadministered with endotoxin as compared to wild type SPE-C activity at the same dose. More preferably, none of the animals develop shock.

Optionally, preferred mutants for vaccine compositions also are further screened and selected for a change in T cell mitogenicity. A change in T-cell mitogenicity can be detected by measuring T-cell proliferation in a standard 3H thymidine assay using rabbit lymphocytes as described in Example 3; by measuring levels of production of cytokines such as IFN gamma or TNF-β; by determining the Vβ type of T cell response or by determining the interaction of the molecules with MHC class II receptors. The preferred method for detecting a decrease in T-cell mitogenicity is to measure T-cell proliferation of rabbit lymphocytes in the presence and absence of the mutant toxin. Responses of T cells to wild type SPE-C toxin is greatly enhanced above a normal in vitro response to an antigen. A substantial decrease in T cell mitogenicity is seen when the mutant SPE-C toxin does not stimulate a T cell proliferative response greater than the stimulation with an antigen or negative control. Preferably, a decrease is seen such that the T cell proliferation response to the mutant SPE-C toxin is no more than two-fold above background when measured using rabbit lymphocytes at the same dose as the wild type SPE-C toxin.

Optionally, the mutant SPE-C toxins useful in vaccine compositions are further screened and selected for a decrease in capillary leak in endothelial cells. The preferred method is using porcine aortic endothelial cells as described by Lee et el., J. Infect. Dis. 164:711 (1991). A decrease in capillary leak in the presence of mutant SPE-C toxins can be determined by measuring a decrease in release of a radioactively labeled compound or by a change in the transport of a radioactively labeled compound. A decrease in capillary leak is seen when the release or transport of a radioactively labeled compound is decreased to less than about two fold above background when compared with the activity of a wild type toxin.

The especially preferred mutant SPE-C toxins useful in vaccine compositions are not biologically active compared with proteins that have wild type SPE-C toxin activity. By nonbiologically active, it is meant that the mutant toxin has little or no systemic lethality, has little or no enhancement of endotoxin shock and little or no T cell mitogenicity. Preferably, the mutant SPE-C toxins selected for vaccine compositions substantially lack these biological activities, i.e., they react like a negative control or they stimulate a reaction no more than two-fold above background.

Changes in other biological activities can be detected as follows. Binding to MHC class II molecules can be detected using such methods as described by Jardetzky, Nature 368:711 (1994). Changes in fever can be detected by monitoring temperatures over time after administration of the mutant SPE-C toxins. Changes in the levels of cytokine production in the presence of mutant SPE-C toxins can be measured using methods such as are commercially available and are described by current protocols in immunology. (Ed. Coligan, Kruisbeck, Margulies, Shevach, and Stroker. National Institutes of Health, John Wiley and Sons, Inc.)

The especially preferred mutants for vaccine compositions are mutant SPE-C toxins that immunoreact with polyclonal neutralizing antibodies to wild type SPE-C toxin, are nontoxic, and optionally have a decrease in potentiation of endotoxin shock and a decrease in T-cell mitogenicity.

Advantageously, mutant SPE-C toxins useful in treatment methods can be generated that have more than one change in the amino acid sequence. It would be desirable to have changes at more than one location to minimize any chance of reversion to a molecule having toxicity or lethality. For vaccine compositions, it is desirable that a mutant toxin with multiple changes can still generate a protective immune response against wild type SPE-C and/or immunoreact with neutralizing polyclonal antibodies to wild type SPE-C. For pharmaceutical compositions, it is preferred that mutants with multiple changes are substantially nonlethal while maintaining mitogenicity for T cells. It is especially preferable to have about 2 to 6 changes. Triple mutants are also contemplated in this application.

Mutant toxins of SPE-C are useful to form vaccine compositions. The preferred mutants for vaccine compositions have at least one amino acid change, are nontoxic systemically, and immunoreact with polyclonal neutralizing antibodies to wild type SPE-C.

Mutant toxins are combined with a physiologically acceptable carrier. Physiologically acceptable diluents include physiological saline solutions, and buffered saline solutions at neutral pH such as phosphate buffered saline. Other types of physiological carriers include liposomes or polymers and the like. Optionally, the mutant toxin can be combined with an adjuvant such as Freund's incomplete adjuvant, Freund's Complete adjuvant, alum, monophosphoryl lipid A, alum phosphate or hydroxide, QS-21 and the like. Optionally, the mutant toxins or fragments thereof can be combined with immunomodulators such as interleukins, interferons and the like. Many vaccine formulations are known to those of skill in the art.

The mutant SPE-C toxin or fragment thereof is added to a vaccine formulation in an amount effective to stimulate a protective immune response in an animal to at least one biological activity of wild type SPE-C toxin. Generation of a protective immune response can be measured by the development of antibodies, preferably antibodies that neutralize the wild type SPE-C toxin. Neutralization of wild type SPE-C toxin can be measured including by inhibition of lethality due to wild type SPE-C in animals. In addition, a protective immune response can be detected by measuring a decrease in at least one biological activity of wild type SPE-C toxins such as amelioration or elimination of the symptoms of enhancement of endotoxin shock or STSS. The amounts of the mutant toxin that can form a protective immune response are about 0.1 $\mu$g to 100 mg per kg of body weight more preferably about 1 $\mu$g to about 100 $\mu$g/kg body weight. About 25 $\mu$g/kg of body weight of wild type SPE-C toxin is effective to induce protective immunity in rabbits.

The vaccine compositions are administered to animals such as rabbits, rodents, horses, and humans. The preferred animal is a human.

The mutant SPE-C toxins are also useful to form pharmaceutical compositions. The pharmaceutical compositions are useful in therapeutic situations where a stimulation of T-cell proliferation may be desirable. The preferred mutant SPE-C toxins are those that are nonlethal while maintaining T-cell mitogenicity comparable to wild type SPE-C toxin.

A pharmaceutical composition is formed by combining a mutant SPE-C toxin with a physiologically acceptable carrier such as physiological saline, buffered saline solutions at neutral pH such as phosphate buffered saline. The mutant SPE-C toxin is combined in an amount effective to stimulate T-cell proliferation comparable to wild type SPE-C toxin at the same dose. An enhancement in T-cell responsiveness can be measured using standard 3H thymidine assays with rabbit lymphocytes as well as by measuring T-cell populations in vivo using fluorescence activated T-cell sorters or an assay such as an ELISPOT. The range of effective amounts are 100 ng to 100 mg per kg of body weight, more preferably 1 $\mu$g to 1 mg/kg body weight. For example, these mutant SPE-C toxins could be used either alone or in conjunction with interleukin or interferon therapy.

The invention also includes fragments of SPE-C toxins and fragments of mutant SPE-C toxins. For vaccine compositions, fragments are preferably large enough to stimulate a protective immune response. A minimum size for a B cell epitope is about 4–7 amino acids and for a T cell epitope about 8–12 amino acids. The total size of wild type SPE-C is about 235 amino acids including the leader sequence. Fragments are peptides that are about 4 to 200 amino acids, more preferably about 10–50 amino acids.

Fragments can be a single peptide or include peptides from different locations joined together. Preferably, fragments include one or more of the domains as identified in FIG. 1 and as described herein. It is also preferred that the fragments from mutant SPE-C toxins have at least one change in amino acid sequence and more preferably 1–6 changes in amino acid sequence when compared to a protein substantially corresponding to a wild type SPE-C toxin.

Preferably, fragments are substantially nonlethal systemically. Fragments are screened and selected to have little or no toxicity in rabbits using the miniosmotic pump model at the same or greater dosage than a protein having wild type SPE-C toxin activity as described previously. It is also preferred that the fragment is nontoxic in humans when given a dose comparable to that of a wild type SPE-C toxin.

For vaccine compositions, it is preferred that the fragments include residues from the central $\alpha$ helix and/or the N-terminal $\alpha$ helix. For vaccine compositions, it is preferable that a fragment stimulate a neutralizing antibody response to a protein having wild type SPE-C toxin activity. A fragment can be screened and selected for immunoreactivity with polyclonal neutralizing antibodies to a wild type SPE-C toxin. The fragments can also be used to immunize animals and the antibodies formed tested for neutralization of wild type SPE-C toxin.

For vaccine compositions, especially preferred fragments are further selected and screened to be nonbiologically active. By nonbiologically active, it is meant that the fragment is nonlethal systemically, induces little or no enhancement of endotoxin shock, and induces little or no T cell stimulation. Optionally, the fragment can be screened and selected to have a decrease in capillary leak effect on porcine endothelial cells.

The fragments screened and selected for vaccine compositions can be combined into vaccine formulations and utilized as described previously. Optionally, fragments can be attached to carrier molecules such as bovine serum albumin, human serum albumin, keyhole limpet hemocyanin, tetanus toxoid and the like.

For pharmaceutical compositions, it is preferred that the fragments include amino acid residues in the N-terminal Domain B $\beta$ strands alone or in combination with the central $\alpha$ helix.

For pharmaceutical compositions, it is preferred that the fragments are screened and selected for nonlethality systemically, and optionally for little or no enhancement of endotoxin shock as described previously. It is preferred that the fragments retain T cell mitogenicity similar to the wild type SPE-C toxin. Fragments of a mutant toxin SPE-C can form pharmaceutical compositions as described previously.

Fragments of mutant SPE-C toxin can be prepared using PCR, restriction enzyme digestion and/or ligation, in vitro mutagenesis and chemical synthesis. For smaller fragments chemical synthesis may be desirable.

The fragments of mutant SPE-C toxins can be utilized in the same compositions and methods as described for mutant SPE-C toxins.

B. Methods for Using Mutant SPE-C Toxins, Vaccines Compositions or Pharmaceutical Compositions.

The mutant SPE-C toxins and/or fragments thereof are useful in methods for protecting animals against the effects of wild type SPE-C toxins, ameliorating or treating animals with STSS, inducing enhanced T-cell proliferation and responsiveness, and treating or ameliorating the symptoms of guttate psoriasis, rheumatic fever, or invasive streptococcal infections.

A method for protecting animals against at least one biological activity of wild type SPE-C toxin involves the step of administering a vaccine composition to an animal to establish a protective immune response against at least one biological activity of SPE-C toxin. It is preferred that the protective immune response is neutralizing and protects against lethality or symptoms of STSS. The vaccine composition preferably includes a mutant SPE-C toxin or fragment thereof that has at least one amino acid change, that immunoreacts with polyclonal neutralizing antibodies to wild type SPE-C, and is nonlethal.

The vaccine composition can be administered to an animal in a variety of ways including subcutaneously, intramuscularly, intravenously, intradermally, orally, intranasally, ocularly, intraperitoneally and the like. The preferred route of administration is intramuscularly.

The vaccine compositions can be administered to a variety of animals including rabbits, rodents, horses and humans. The preferred animal is a human.

The vaccine composition can be administered in a single or multiple doses until protective immunity against at least one of the biological activities of wild type SPE-C is established. Protective immunity can be detected by measuring the presence of neutralizing antibodies to the wild type SPE-C using standard methods. An effective amount is administered to establish protective immunity without causing substantial toxicity.

A mutant SPE-C toxin or fragment thereof is also useful to generate neutralizing antibodies that immunoreact with the mutant SPE-C toxin and the wild type SPE-C toxin. These antibodies could be used as a passive immune serum to treat or ameliorate the symptoms in those patients that have the symptoms of STSS. A vaccine composition as described above could be administered to an animal such as a horse or a human until a neutralizing antibody response to wild type SPE-C is generated. These neutralizing antibodies can then be harvested, purified, and utilized to treat patients exhibiting symptoms of STSS. Neutralizing antibodies to wild type SPE-C toxin can also be formed using wild type SPE-C. However, wild type SPE-C must be administered at a dose much lower than that which induces toxicity such as 1/50 to 1/100 of the LD50 of wild type SPE-C in rabbits.

The neutralizing antibodies are administered to patients exhibiting symptoms of STSS such as fever, hypotension, group A streptococcal infection, myositis, fascitis, and liver damage in an amount effective to neutralize the effect of SPE-C toxin. The neutralizing antibodies can be administered intravenously, intramuscularly, intradermally, subcutaneously, and the like. The preferred route is intravenously or for localized infection, topically at the site of tissue damage with debridement. It is also preferred that the neutralizing antibody be administered in conjunction with antibiotic therapy. The neutralizing antibody can be administered until a decrease in shock or tissue damage is obtained in a single or multiple dose. The preferred amount of neutralizing antibodies typically administered is about 1 mg to 1000 mg/kg, more preferably about 50–200 mg/kg of body weight.

C. DNA Expression Cassettes Encoding Mutant SPE-C Toxins and Methods of Preparation of Such DNA Expression Cassettes The invention also includes DNA sequences and expression cassettes useful in expression of mutant SPE-C toxins and/or fragments thereof. An expression cassette includes a DNA sequence encoding a mutant SPE-C toxin and/or fragment thereof with at least one amino acid change and at least one change in biological function compared to a protein substantially corresponding to a wild type SPE-C toxin operably linked to a promoter functional in a host cell. Expression cassettes are incorporated into transformation vectors and mutant SPE-C toxins are produced in transformed cells. The mutant toxins can then be purified from host cells or host cell supernatants. Transformed host cells are also useful as vaccine compositions.

Mutant SPE-C toxins or fragments thereof can also be formed by screening and selecting for spontaneous mutants in a similar manner as described for site specific or random mutagenesis. Mutant SPE-C toxins can be generated using in vitro mutagenesis or semisynthetically from fragments produced by any procedure. Finally, mutant SPE-C toxins can be generated using chemical synthesis.

A method of producing the mutant SPE-C toxins or fragments thereof which includes transforming or transfecting a host cell with a vector including such an expression cassette and culturing the host cell under conditions which permit expression of such mutant SPE-C toxins or fragments by the host cell.

DNA Sequences Encoding Mutant SPE-C Toxins

A mutant DNA sequence encoding a mutant SPE-C toxin that has at least one change in amino acid sequence can be formed by a variety of methods depending on the type of change selected. A DNA sequence encoding a protein substantially corresponding to wild type SPE-C toxin functions as template DNA used to generate DNA sequences encoding mutant SPE-C toxins. A DNA sequence encoding wild type SPE-C toxin is shown in FIG. 1.

To make a specific change or changes at a specific location or locations it is preferred that PCR is utilized according to method of Perrin et al., cited supra. To target a change to a particular location, internal primers including the altered nucleotides coding for the amino acid change are included in a mixture also including a 5' and 3' flanking primers. A 5' flanking primer is homologous to or hybridizes to a DNA region upstream of the translation start site of the coding sequence for wild type SPE-C. Preferably, the 5' flanking region is upstream of the speA promoter and regulatory region. For example, a 5' flanking primer can be homologous to or hybridize to a region about 760 bases upstream of the translation start site. A downstream flanking primer is homologous to or hybridizes to a region of DNA downstream of the stop codon of the coding sequence for wild type SPE-C. It is preferred that the downstream flanking primer provides for transcriptional and translational termination signals. For example, a 3' flanking primer can hybridize or be homologous to a region 200 base pairs downstream of the stop codon for the coding sequence of SPE-C. The upstream and downstream flanking primers are present in every PCR reaction to ensure that the resulting PCR product includes the speC promoter and upstream regulatory region and transcriptional and translation termination signals. Other upstream and downstream primers can readily be constructed by one of skill in the art. While preferred, it is not absolutely necessary that the native speC promoter and upstream regulatory region be included in the PCR product.

Internal primers can be designed to generate a change at a specific location utilizing a DNA sequence encoding wild type SPE-C. Primers can be designed to encode a specific amino acid substitution at a specific location. Primers can be designed to result in random substitution at a particular site as described by Rennell et al., J. Mol. Biol. 22:67 (1991). Primers can be designed that result in a deletion of an amino acid at a particular site. Primers can also be designed to add coding sequence for an additional amino acid at a particular location.

Primers are preferably about 15 to 50 nucleotides long, more preferably 15 to 30 nucleotides long. Primers are preferably prepared by automated synthesis. The 5' and 3' flanking primers preferably hybridize to the flanking DNA sequences encoding the coding sequence for the wild type SPE-C toxin. These flanking primers preferably include about 10 nucleotides that are 100% homologous or complementary to the flanking DNA sequences. Internal primers are not 100% complementary to DNA sequence coding for the amino acids at location because they encode a change at that location. An internal primer can have about 1 to 4 mismatches from the wild type SPE-C sequence in a primer about 15 to 30 nucleotides long. Both flanking primers and internal primers can also include additional nucleotides that encode for restriction sites and clamp sites, preferably near the end of the primer. Hybridization conditions can be modified to take into account the number of mismatches present in the primer in accord with known principles as described by Sambrook et al. Molecular Cloning-A laboratory manual, Cold Spring Harbor Laboratory Press, (1989).

More than one internal primer can be utilized if changes at more than one site are desired. A PCR method for generating site-specific changes at more than one location is described in Aiyar et al. cited supra. Another method is described in Example 5.

In one method, a DNA sequence encoding a mutant SPE-C toxin with one change at a particular site is generated and is then used as the template to generate a mutant DNA sequence with a change at a second site. In the first round of PCR, a first internal primer is used to generate the mutant DNA sequence with the first change. The mutant DNA sequence with the first change is then used as the template DNA and a second internal primer coding for a change at a different site is used to form a DNA sequence encoding a mutant toxin with changes in amino acid sequences at two locations. PCR methods can be utilized to generate DNA sequences with encoding amino acid sequences with about 2 to 6 changes.

A preferred PCR method is as described by Perrin et al. cited supra. Briefly, the PCR reaction conditions are: PCR is performed in a 100 ul reaction mixture containing 10 mM Tris-HCl (pH=8.3), 50 mM KCl, 1.5 mM MgCl2, 200 uM each dNTP, 2 ng template plasmid DNA, 100 pmoles flanking primer, 5 pmoles internal primer, and 2.5 units of Ampli Taq DNA polymerase (Perkin Elmer Cetus). In the second amplification step, the composition of the reaction mix is as above except for equal molarity (5 pmoles each) of flanking primer and megaprimer and 1 ug template. PCR is conducted for 30 cycles of denaturation at 94° C.×1 minute, annealing at 37° C. or 44° C.×2minutes and elongation at 72° C. for 3 minutes.

The PCR products are isolated and then cloned into a shuttle vector (such as pMIN 164 as constructed by the method of Murray et al, J. Immunology 152:87 (1994) and available from Dr. Schlievert, University of Minnesota, Mpls, Minn.). This vector is a chimera of E. coli plasmid pBR328 which carries ampicillin resistance and the staphylococcal plasmid pE194 which confers erythromycin resistance. The ligated plasmid mixtures are screened in E. coli for toxin production using polylconal neutralizing antibodies to wild type SPE-C from Toxin Technologies, Boca Raton, Fla. or from Dr. Schlievert. The mutant SPE-C toxins are sequenced by the method of Hsiao et al., Nucleic Acid Res. 19:2787 (1991) to confirm the presence of the desired mutation and absence of other mutations.

It will be understood by those of skill in the art that due to the degeneracy of the genetic code a number of DNA sequences can encode the same changes in amino acids. The invention includes DNA sequences having different nucleotide sequences but that code for the same change in amino acid sequence.

For random mutagenesis at a particular site a series of primers are designed that result in substitution of each of the other 19 amino acids or a non-naturally occurring amino acid or analog at a particular site. PCR is conducted in a similar manner as described above or by the method described by Rennell et al., cited supra. PCR products are subcloned and then toxin production can be monitored by immunoreactivity with polylconal neutralizing antibodies to wild type SPE-C. The presence of a change in amino acid sequence can be verified by sequencing of the DNA sequence encoding the mutant SPE-C toxin. Preferably, mutant toxins are screened and selected for nonlethality.

Other methods of mutagenesis can also be employed to generate random mutations in the DNA sequence encoding the wild type SPE-C toxin. Random mutations or random mutagenesis as used in this context means mutations are not at a selected site and/or are not a selected change. A bacterial host cell including a DNA sequence encoding the wild type SPE-C toxin can be mutagenized using other standard methods such as chemical mutagenesis, and UV irradiation. Mutants generated in this manner can be screened for toxin production using polyclonal neutralizing antibodies to wild type SPE-C. However, further screening is necessary to identify mutant toxins that have at least one change in a biological activity, preferably that are nonlethal. Spontaneously arising mutants can also be screened for at least one change in a biological activity from wild type SPE-C.

Random mutagenesis can also be conducted using in vitro mutagenesis as described by Anthony-Cahill et al., Trends Biochem. Sci. 14: 400 (1989).

In addition, mutant SPE-C toxins can be formed using chemical synthesis. A method of synthesizing a protein chemically is described in Wallace, FASEB J. 7:505 (1993). Parts of the protein can be synthesized and then joined together using enzymes or direct chemical condensation. Using chemical synthesis would be especially useful to allow one of skill in the art to insert non-naturally occurring amino acids at desired locations. In addition, chemical synthesis would be especially useful for making fragments of mutant SPE-C toxins.

Any of the methods described herein would be useful to form fragments of mutant SPE-C toxins. In addition, fragments could be readily generated using restriction enzyme digestion and/or ligation. The preferred method for generating fragments is through direct chemical synthesis for fragment of 20 amino acids or less or through genetic cloning for larger fragments.

DNA sequences encoding mutant toxins, whether site-specific or random, can be further screened for other changes in biological activity from wild type SPE-C toxin. The methods for screening for a change in at least one biological activity are described previously. Once selected DNA sequences encoding mutant SPE-C toxins are selected for at least one change in biological activity, they are utilized to form an expression cassette.

Formation of an expression cassette involves combining the DNA sequences coding for mutant SPE-C toxin with a promoter that provides for expression of a mutant SPE-C toxin in a host cell. For those mutant SPE-C toxins produced using PCR as described herein, the native speC promoter is present and provides for expression in a host cell.

Optionally, the DNA sequence can be combined with a different promoter to provide for expression in a particular type of host cell or to enhance the level of expression in a host cell. Preferably, the promoter provides for a level of expression of the mutant SPE-C toxin so that it can be detected with antibodies to SPE-C. Other promoters that can be utilized in prokaryotic cells include PLAC, PTAC, T7, and the like.

Once the DNA sequence encoding the mutant SPE-C toxin is combined with a suitable promoter to form an expression cassette, the expression cassette is subcloned into a suitable transformation vector. Suitable transformation vectors include at least one selectable marker gene and preferably are shuttle vectors that can be amplified in *E. coli* and gram positive microorganisms. Examples of suitable shuttle vectors include pMIN 164, and pCE 104. Other types of vectors include viral vectors such as the baculovirus vector, SV40, poxviruses such as vaccinia, adenovirus and cytomegalovirus. The preferred vector is a pMIN 164 vector, a shuttle vector that can be amplified in *E. coli* and *S. aureus*.

Once a transformation vector is formed carrying an expression cassette coding for a mutant SPE-C toxin, it is introduced into a suitable host cell that provides for expression of the mutant SPE-C toxin. Suitable host cells are cells that provide for high level of expression of the mutant toxin while minimizing the possibility of contamination with other undesirable molecules such as endotoxin and M-proteins. Suitable host cells include mammalian cells, bacterial cells such as *S. aureus, E. coli* and *Salmonella* spp., yeast cells, and insect cells.

Transformation methods are known to those of skill in the art and include protoplast transformation, liposome mediated transformation, calcium phosphate precipitation and electroporation. The preferred method is protoplast transformation.

Transformed cells are useful to produce large amounts of mutant SPE-C toxin that can be utilized in vaccine compositions. A transformed microorganism can be utilized in a live, attenuated, or heat killed vaccine. A transformed microorganism includes mutant toxin SPE-C in amounts sufficient to stimulate a protective immune response to wild type SPE-C. Preferably, the mutant SPE-C toxin is secreted. The microorganism is preferably nonpathogenic to humans and includes a mutant toxin with multiple amino acid changes to minimize reversion to a toxic form. The microorganism would be administered either as a live or heat killed vaccine in accordance with known principles. Preferred microorganisms for live vaccines are transformed cells such as *Salmonella* spp.

A viral vector including an expression cassette with a DNA sequence encoding a mutant SPE-C toxin or fragment thereof operably linked to a promoter functional in a host cell can also be utilized in a vaccine composition as described herein. Preferably, the promoter is functional in a mammalian cell. An example of a suitable viral vector includes pox viruses such as vaccinia virus, adenoviruses, cytomegaloviruses and the like. Vaccinia virus vectors could be utilized to immunize humans against at least one biological activity of a wild type SPE-C toxin.

The invention also includes a vaccine composition comprising an nucleic acid sequence encoding a mutant SPE-C toxin or fragment thereof operably linked to a promoter functional in a host cell. The promoter is preferably functional in a mammalian host cell. The nucleic acid sequence can be DNA or RNA. The vaccine composition is delivered to a host cell or individual for expression of the mutant SPE C toxin or fragment thereof within the individuals own cells. Expression of nucleic acid sequences of the mutant SPE C toxin or fragment thereof in the individual provides for a protective immune response against the wild type SPE C toxin. Optionally, the expression cassette can be incorporated into a vector. A nucleic acid molecule can be administered either directly or in a viral vector. The vaccine composition can also optionally include a delivery agent that provides for delivery of the vaccine intracellularly such as liposomes and the like. The vaccine composition can also optionally include adjuvants or other immunomodulatory compounds, and additional compounds that enhance the uptake of nucleic acids into cells. The vaccine composition can be administered by a variety of routes including parenteral routes such as intravenously, intraperitoneally, or by contact with mucosal surfaces.

Conditions for large scale growth and production of mutant SPE-C toxin are known to those of skill in the art. A method for purification of mutant SPE-C toxins from microbial sources is as follows. *S. aureus* carrying the mutant or the wild type speCs in pMIN164 are grown at 37° C. with aeration to stationary phase in dialyzable beef heart medium, containing 5 μg/ml of erythromycin. Cultures are precipitated with four volumes of ethanol and proteins resolubilized in pyrogen free water. The crude preparations are subjected to successive flat bed isoelectric focusing separations in pH gradients of 3.5 to 10 and 4 to 6. The fractions that are positive for toxin by antibody reactivity are extensively dialyzed against pyrogen free water, and an aliquot of each is tested for purity by SDS polyacrylamide gel electrophoresis in 15% (weight/volume) gels. Polyclonal neutralizing antibodies to SPE-C are available from Toxin Technologies, Boca Raton, Fla. or Dr. Schlievert. Other methods of purification including column chromatography or HPLC can be utilized.

This invention can be better understood by way of the following examples which are representative of the preferred embodiments thereof, but which are not to be construed as limiting the scope of the invention.

EXAMPLE 1

Cloning and Expression of SPE-C Wild Type
Cloning and Expression of speC in *E. coli*

To obviate the need of toxin detection for gene isolation, oligonucleotides specific for the SPE-C gene were synthesized and used to screen a streptococcal genomic library. Purified streptococcal DNA from strain T18P was partially digested with the restriction endonuclease Sau 3A and separated on 0.7% agarose gel. Fragments in the 4–8 kilobase range were eluted from the gel and ligated to vector plasmid pBR328, which had been linearized with BAMHI and dephosphorylated to prevent self-ligation. The ligated DNA was then used to transform competent *E. coli* RR1 cells to ampicillin resistance. Transformants were grown on nitrocellulose filters overlayed on LB agar containing ampicillin. Replica filters were prepared, and approximately 1500 recombinant colonies were screened for the presence of the speC gene by colony hybridization to radiolabeled synthetic oligonucleotides. Two families of mixed sequence oligonucleotides were derived from the hexapeptide sequence, Asp-Ser-Lys-Lys-Asp-Ile, which corresponds to the first six amino acids of the amino terminus of the mature SPE-C protein (FIG. 1). The oligonucleotides were split into two families to control the redundancy of the probes and thereby minimize nonspecific hybridization. Two colonies were found to hybridize with oligonucleotide family A. Colonies hybridizing to family B were not found. The hybridizing clones were assayed for SPE-C expression by precipitation with SPE-C antiserum in Ouchterlony immunodiffusion tests. The lysate from one of the selected clones formed a precipitin line of identity with purified SPE-C. The recombinant plasmid containing speC was designated pUMN 501. Culture supernatant fluid from RR1pUMN 501 was found not to contain detectable amounts of SPE-C, suggesting that *E. coli* was unable to secrete the toxin.

Subcloning

The insert within pUMN 501 was approximately 4.0 kilobases and bordered by Sau 3A sites (FIG. 2). Digestion with XbaI yielded a 2.4 and a 1.6 kilobase fragment, neither of which directed speC expression when ligated to pUC13 and transformed into *E. coli* JM101 (pUMN 512 and pUMN 511, respectively). The larger Sau 3A-SalI fragment (3.3 kilobases) expressed speC in *E. coli* JM101 pUMN 513). The gene was expressed in either orientation with respect to the plasmid promoter, suggesting that the native streptococcal promoter was present within the insert and functional in *E. coli*. The speC gene was further localized by cloning a 3.3 kilobase Sau 3A-SalI fragment into M13 bacteriophage and utilizing the procedure of Dale et al. Plasmid 13:31–40 (1985) to generate deletion subclones. A 1.7 kilobase fragment isolated from an M13 subclone and ligated to pUC13 (pUMN 521), was capable of expression speC in *E. coli*.

EXAMPLE 2

Biochemical Characterization of *E. coli*-derived SPE-C

SPE-C encoded by UMN 501 was partially purified from extracts of *E. coli* RR1 by ethanol precipitation followed by preparative isoelectric focusing in a pH gradient of 3.5–10. *E. coli*-derived toxin migrated to the same approximate location, (between 6.5 and 7.2), as the streptococcal-derived toxin. *E. coli* and streptococcal-derived SPE-C had identical molecular weights of 24000 in SDS-PAGE. Though additional proteins were present in the *E. coli* preparation, only the 24000 mw protein reacted when tested by an immunoblot technique using SPE-C-specific antiserum.

EXAMPLE 3

Biological Characterization of *E. coli*-derived SPE-C

*E. coli* and streptococcal-derived SPE-C were compared for lymphocyte mitogenicity. Rabbit splenocytes ($2\times10^5$ cells) were exposed to approximately 0.01 ug SPE-C from *S. pyogenes* or *E. coli*(pUMN 501). After 3 days, the cultures were pulsed with 1 uCi [$^3$H]-thymidine and incubated for 24 h, after which incorporation of radiolabel into cellular DNA was quantified. Both toxin preparations induced a similar mitogenic response. Incubation with SPE-C antiserum significantly reduced the mitogenic response of both cloned and streptococcal-derived toxin.

Streptococcal and *E. coli*-derived SPE-C were also compared for pyrogenicity and enhancement of lethal endotoxin shock in rabbits. The streptococcal and *E. coli*-derived SPE-C were equally pyrogenic; the average rise in temperature for both preparations was 1.0 C after 4 h. The fever responses were monophasic, rather than biphasic as is characteristic of endotoxin. This suggests that the fever was attributable to SPE-C and not due to endotoxin contamination. Both *E. coli* and streptococcal-derived SPE-C treated animals showed enhanced susceptibility to endotoxin shock. All of the control rabbits receiving only PBS and endotoxin, survived.

These studies confirm that SPE-C is expressed in *E. coli* in a biologically active form, and activities attributed to SPE-C were not due to a copurified streptococcal contaminant.

EXAMPLE 4

Administration and Immunization of Rabbits with Recombinantly Produced SPE-C (wt)

Recombinantly produced SPE-C was administered to rabbits at a total dose of 200 µg/in 0.2 ml over a 7-day period. The results indicate that animals treated with SPE-C developed the criteria of STSS with nearly all animals succumbing in the 7-day period (data not shown). The symptoms of STSS in rabbits include weight loss, diarrhea, mottled face, fever, red conjunctiva and mucosa, and clear brown urine. As expected, control non-toxin treated animals remained healthy. Two other major observations were made: 1) fluid replacement provided complete protection to the animals as expected, and 2) none of the toxin treated animals developed necrotizing fascitis and myositis, indicating factors other than, or in addition to, SPE-C are required for the soft tissue damage. Development of the clinical features of STSS correlates with administration of SPE-C.

EXAMPLE 5

Preparation of Double or Triple Mutants of SPE-C Using PCR

There are a number of methods that are used to generate double or triple mutant SPE-C toxins or fragments thereof.

Mutant SPE-C toxins with two or more changes in amino acid sequences are prepared using PCR as described previously. In a first PCR reaction, a first internal primer coding for the first change at a selected site was combined with 5'and 3' flanking primers to form a first PCR product. The first PCR product was a DNA sequence coding for a mutant SPE-C toxin having one change in amino acid sequence. This first PCR product then served as the template DNA to generate a second PCR product with two changes in amino acid sequence compared with a protein having wild type SPE-C activity. The first PCR product was the template DNA combined with a second internal primer coding for a change in amino acid at a second site. The second internal primer was also combined with the 5' and 3' flanking primers to form a second PCR product. The second PCR product was a DNA sequence encoding a mutant SPE-C toxin with changes at two sites in the amino acid sequence. This second PCR product was then used as a template in a third reaction to form a product DNA sequence encoding a mutant SPE-C toxin with changes at three sites in the amino acid sequence. This method is utilized to generate DNA sequences encoding mutant toxins having more than one change in the amino acid sequence.

An alternative method to prepare DNA sequences encoding more than one change is to prepare fragments of DNA sequence encoding the change or changes in amino acid sequence by automated synthesis. The fragments are then subcloned into the wild type SPE-C coding sequence using several unique restriction sites. Restriction sites are known to those of skill of the art and are readily determined from the DNA sequence of a wild type SPE-C toxin. The cloning is done in a single step with a three fragment ligation method as described by Revi et al. Nucleic Acid Res. 16:1030 (1988).

EXAMPLE 6

Evaluation of Single and Double Mutants of SPE-C
Serine Mutants

Three single amino acid mutants of SPE C were made: a) Y15S in which tyrosine at position 15 was changed to serine, b) Y17S in which tyrosine at position 17 was changed to serine, c) N38S in which asparagine at position 38 as changed to serine. Two double amino acid mutants of SPE C also were made: a) Y15S/N38S, b) Y17S/N38S. All mutants were constructed by use of the Quik Change method (Stratagene, La Jolla, Calif.) with the speC containing plasmid pUMN521 as template. pUMN521 contains the SPE C gene (speC) in pUC13 (Goshorn et al.).

The single amino acid mutant proteins were produced in *Escherichia coli* in 100 ml cultures. After growth in the presence of 50 µg/ml ampicillin, the *E. coli* cultures were treated with 400 ml −20° C. ethanol to lyse cells and precipitate SPE C mutant proteins. pUMN521 in *E. coli* was treated comparably for use as a positive control. The precipitates were collected and restored to 1 ml. Toxin concentrations were estimated to be 25 µg/ml.

Figure 7:
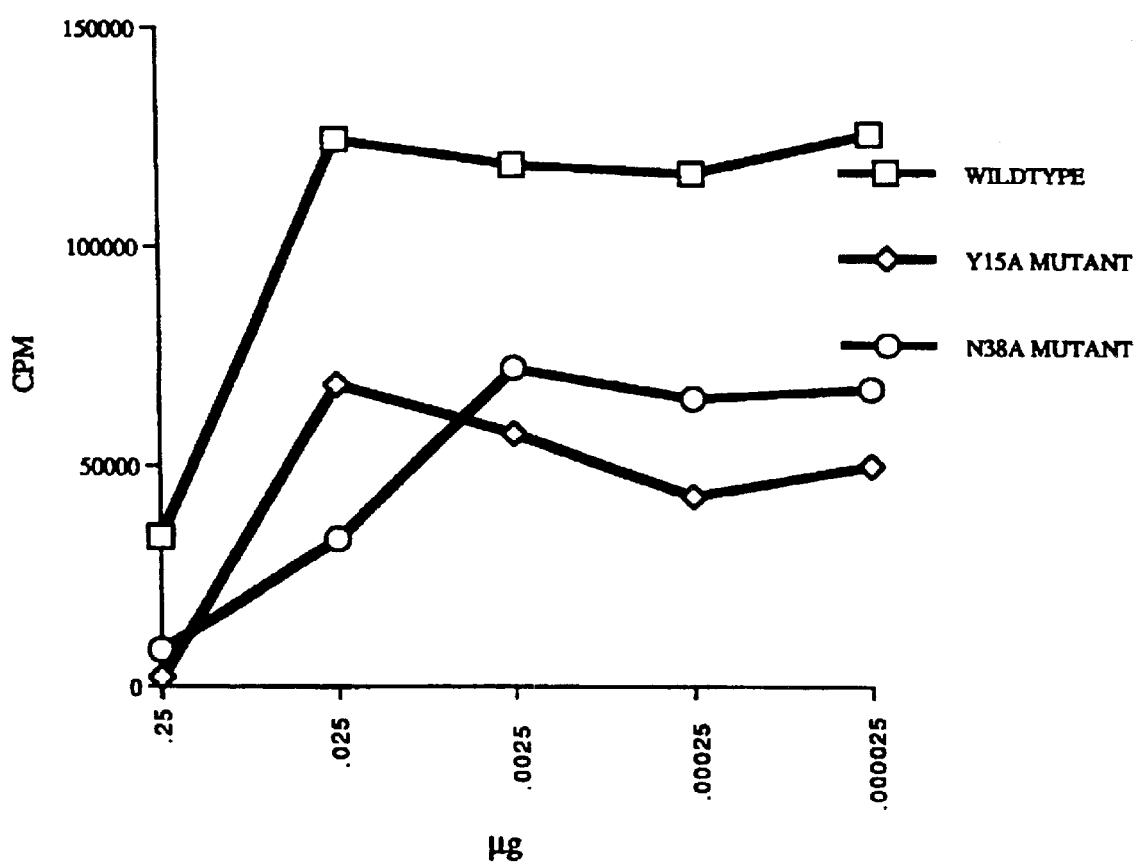
FIG. 7 shows mitogenic activity of single mutants Y15A and N38A.
Figure 8:
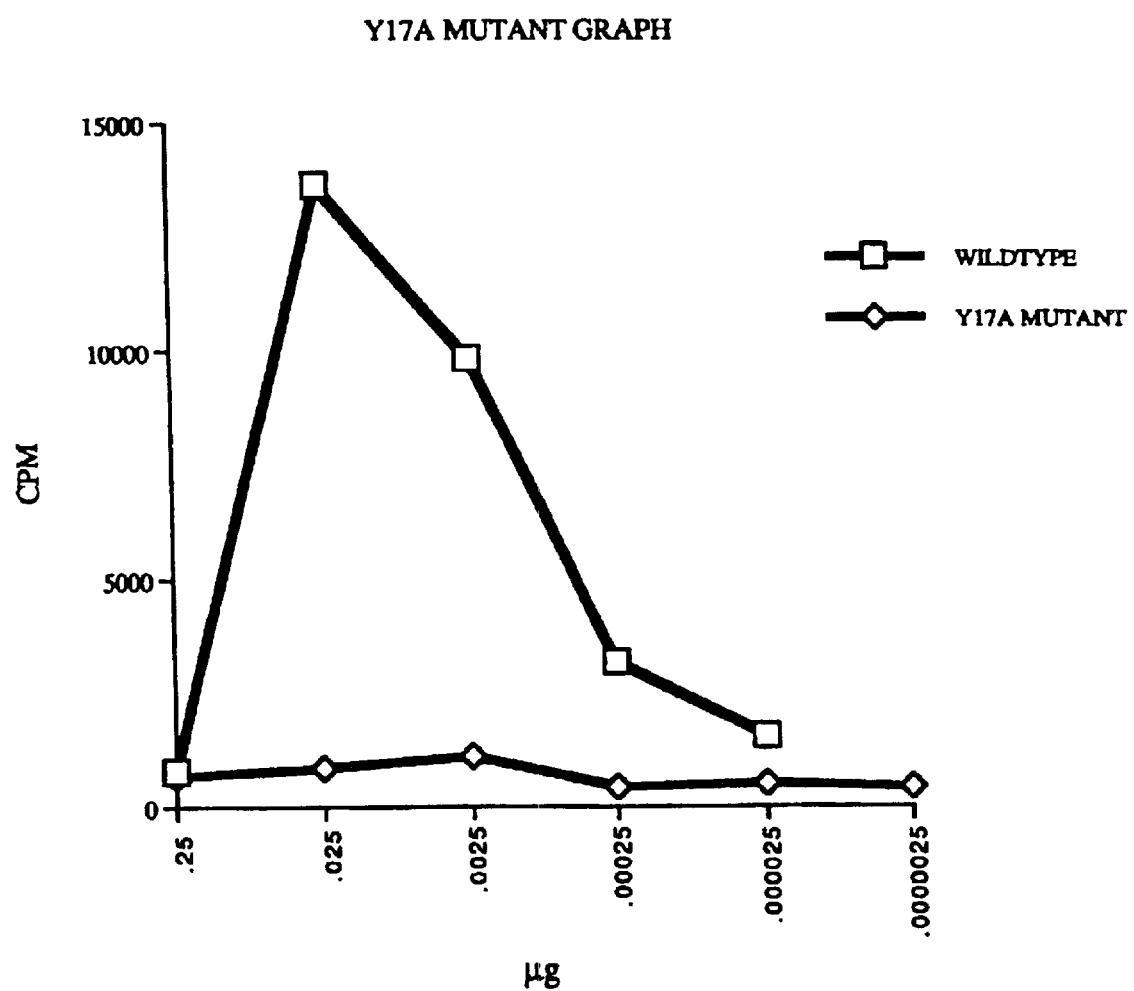
FIG. 8 shows mitogenic activity of single mutants Y17A.

Wild type SPE C from pUMN521 and the three single amino acid mutants were evaluated for capacity to induce rabbit splenocyte proliferation over a toxin dose range of 0.25 to $2.5 \times 10^{-5}$ or $2.5 \times 10^{-6}$. As indicated in FIG. 7, the Y15S and N38S mutants were approximately one half as mitogenic as the wild type. The Y17S mutant was essentially nonmitogenic (FIG. 8).

Figure 9:
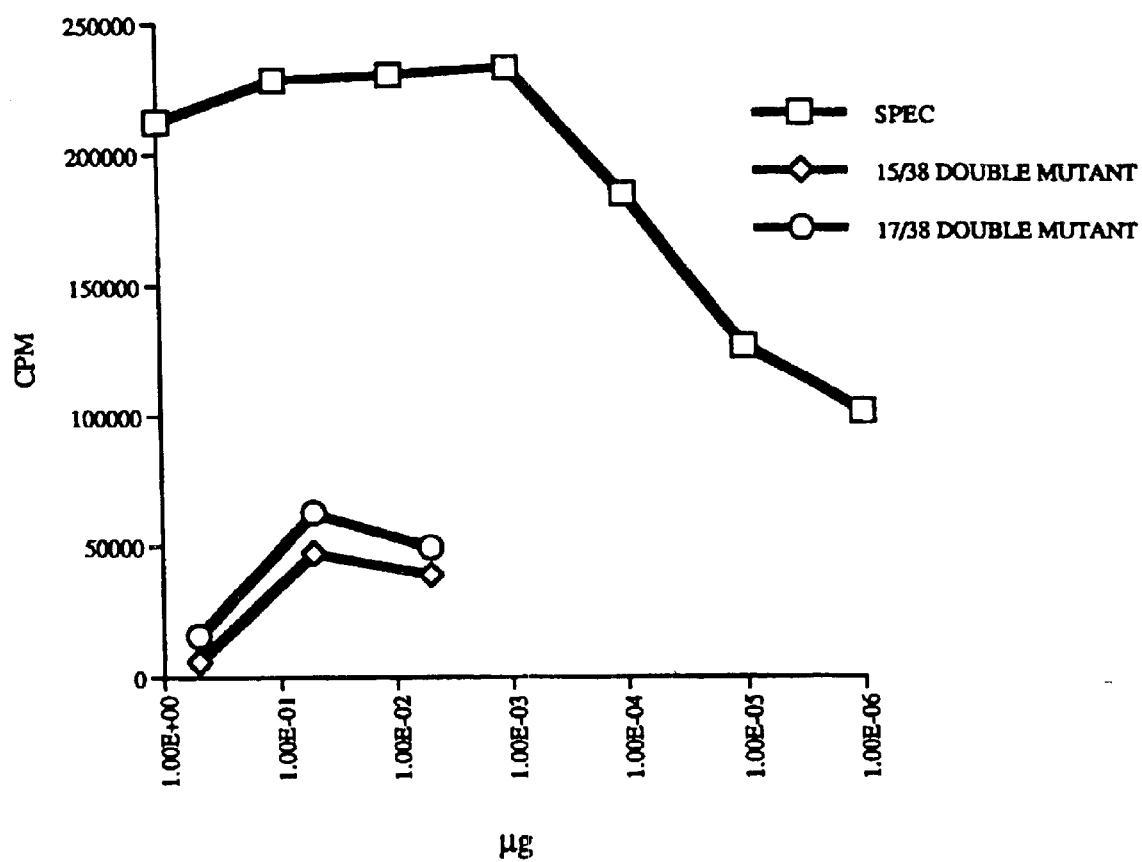
FIG. 9 shows mitogenic activity of double mutants Y15A/N38A and Y17A/N38A.
Figure 10:
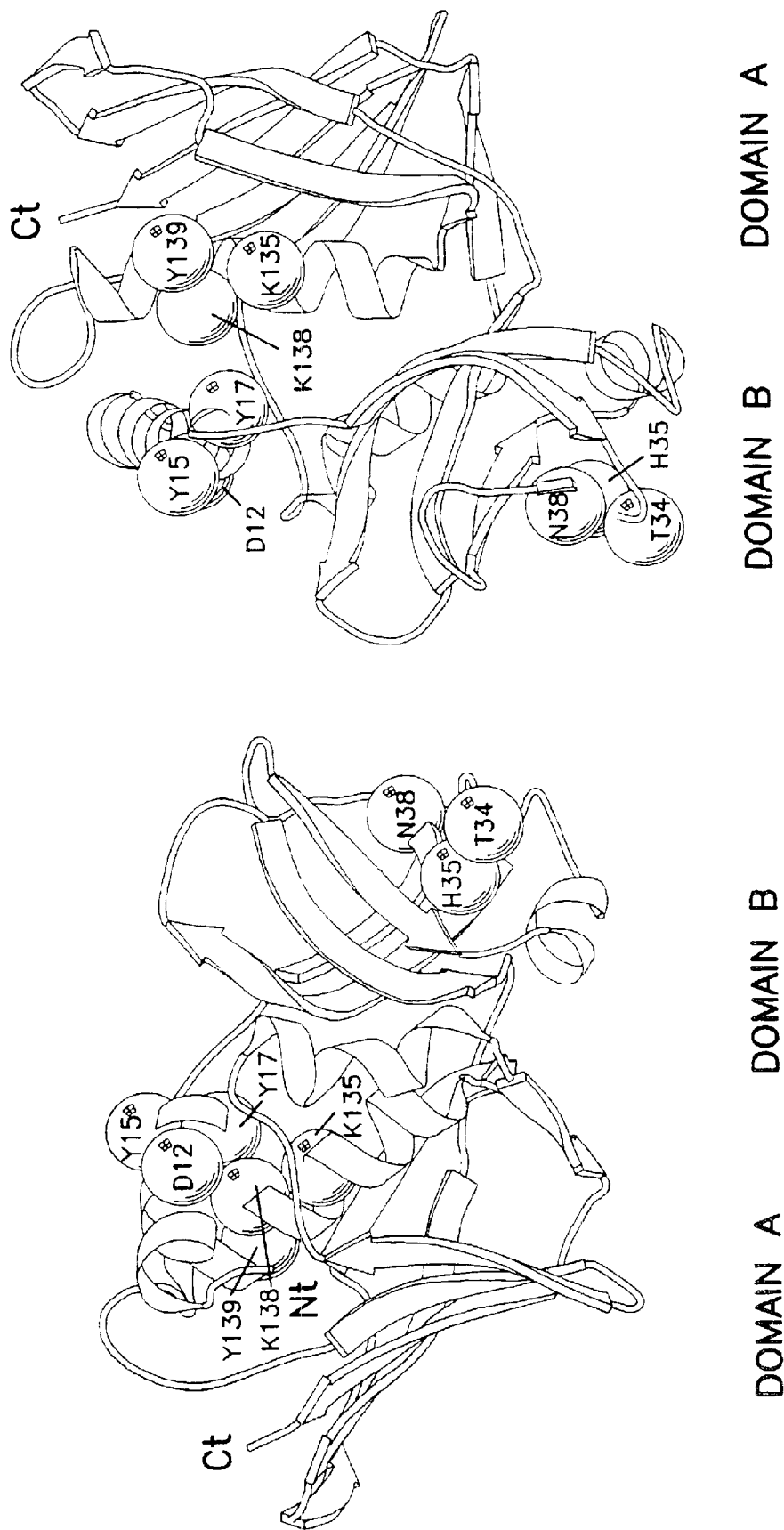
FIG. 10 shows front and back views of a ribbon structure of SPE-C showing residues substituted in Example 6.

The double mutants Y15S/N38S and Y17S/N38S were also tested for ability to stimulate rabbit splenocytes compared to wild type toxin (FIG. 9). Both mutants stimulated rabbit splenocytes only to one-fourth that seen by comparable amounts of wild type toxin.

Both double mutants were also tested for capacity to enhance endotoxin shock. Three rabbits/group were challenged intravenously with 5 µg/kg of mutants or wild type toxin. After 4 hours, the same animals were challenged with 10 µg/kg *Salmonella typhimurium* endotoxin (1/50 $LD_{50}$). Deaths were recorded over a 48 hour time period (Table 4). As indicated, neither double mutant caused lethality in the rabbits.

TABLE 4

Capacity of double amino acid mutants of SPE C to enhance rabbit susceptibility to endotoxin shock.

| Treatment Protein | Number Dead Total Rabbits tested |
|---|---|
| SPE C wild type | 3/3 |
| Y15S/N38S | 0/3 |
| Y17S/N38A | 0/3 |

Note: In the study reported in Table 4, all rabbits were challenged intravenously with 5 µg/kg protein and then 4 hours later with endotoxin (10 µg/kg).

One week after challenge of the rabbits used in Table 4, the animals were euthanized and examined for gross tissue damage. All organs, including liver, spleen, kidneys, lungs and heart appeared normal. This is consistent with the lack of toxicity of the double mutants.

Three rabbits/group were also immunized with two weekly doses of 25 µg of SPE C double mutants emulsified in Freund's incomplete adjuvant. The animals were then rested for 5 days. 0.5 ml of blood was collected from each animal and pooled for collection of Y15S/N38S and Y17S/N38S sera. The sera from these pools was compared to preimmune pooled serum by peroxidase based ELISA (Hudson and Hay reference) for antibodies against purified streptococcal derived wild type SPE C. Table 5 summarizes the results of the ELISA.

TABLE 5

ELISA antibody titers of rabbits immunized against Y15S/N38S and Y17S/N38S mutants of SPE C.*

|  | Sample tested | ELISA titer: |
|---|---|---|
| Y15S/N38S | Preimmune | <10* |
|  | Immune | 80 |
| Y17S/N38S | Preimmune | <10 |
|  | Immune | 80 |

*Sera to be tested for antibody were diluted 2-fold beginning at 1:10. The titer of antibody is the reciprocal of the last dilution that gave an absorbency at 490 nm of 0.1 or greater.

The immunized animals were then challenged with 5 µg/kg of wild type SPE C and then 4 hours later 10 µg/kg of *Salmonella typhimurium* endotoxin as a test for capacity to immunize against lethality. Table 6 indicates the animals were protected from challenge and were thus immune to SPE C.

TABLE 6

Challenge of Y15S/N38S and Y17S/N38S immune animals with wild type SPE C and endotoxin.

| Rabbit Group | Number Dead/Total Tested |
|---|---|
| Nonimmune | 2/2 |
| Y15S/N38S immune | 0/3 |
| Y17S/N38S immune | 0/3 |

Additional single amino acid mutants of SPE C were also prepared. These include residues in the three major domains that may be required for toxicity. These include the T cell receptor binding domain, the class II MHC binding domain, and residues along the back of the central diagonal alpha helix. The residues changed and the effect of the mutation on T cell miotgenicity are listed in Table 7.

TABLE 7

Effect of mutants of SPE C on T lymphocyte mitogenicity and lethality

|  | Biological Activity | |
|---|---|---|
| Mutant | Mitogenicity[a] | Lethality[b] |
| D12A | Not tested | 0/2 |
| H35A | 100% of wild type | Not tested |
| N38D | Not Tested | 0/2 |
| K135D | 50% of wild type | Not tested |
| K138D | 62% of wild type | Not tested |
| Y139A | 54% of wild type | Not tested |
| D142N | 52% of wild type | Not tested |

[a]Comparison made at 0.1 µg/well dose.
[b]Number of rabbits that succumbed/total injected due to enhanced susceptibility to endotoxin; 2/2 animals that received wild type SPE C died.

Alanine Mutants

Two single amino acid mutants of SPE C were made: a) Y15A in which tyrosine at position 15 was changed to alanine and b) Y17A in which tyrosine at position 17 was changed to alanine. Two double amino acid mutants of SPE C also were made: a) Y15A/N38A and b) Y17A/N38A, in which N38A designates a mutant in which asparagine at position 38 was changed to alanine. All mutants were constructed by use of the Quik Change method (Stratagene, La Jolla, Calif.) with the speC containing plasmid pUMN521 as template. pUMN521 contains the SPE C gene (speC) in pUC13 (Goshorn et al.).

The single amino acid mutant proteins were produced in *Escherichia coli* in 100 ml cultures. After growth in the presence of 50 µg/ml ampicillin the *E. coli* cultures were treated with 400 ml −20° C. ethanol to lyse cells and precipitate SPE C mutant proteins. pUMN521 in *E. coli* was treated comparably for use as a positive control. The precipitates were collected and restored to 1 ml. Toxin concentrations were estimated to be 25 µg/ml.

Wild type SPE C from pUMN521 and the two single amino acid mutants were evaluated for capacity to induce rabbit splenocyte proliferation over a toxin dose range of 0.25 to $2.5 \times 10^{-5}$ or $2.5 \times 10^{-6}$. The Y15A and Y17A mutants were essentially nonmintogenic (FIG. 8).

The double mutants Y15A/N38A and Y17A/N38A were also tested for ability to stimulate rabbit splenocytes compared to wild type toxin. Both mutants stimulated rabbit splenocytes only to less than one-sixth that seen by comparable amounts of wild type toxin.

Each of the mutants was also tested for capacity to enhance endotoxin shock. Two rabbits/group were challenged intravenously with about 25 µg/kg of mutants or 5 µg/kg wild type toxin (derived from Group A Streptococcal strain T18P). Temperatures were monitored rectally. (Table 8). Then the rabbits were challenged intravenously with 5 µg/rabbit of *Salmonella typhimurium* endotoxin. Deaths were recorded over a 48 hour time period (Table 8). As indicated, neither double mutant nor the Y15A mutant caused lethality in the rabbits. Each of the mutants reduced fever.

TABLE 8

Toxicity of Alanine Mutants Compared to Wild Type

| SPEC C | Pyrogenicity - Δ° C. at 4 hr. | Dead/ Total |
|---|---|---|
| Wild Type | 1.65 | 2/2 |
| Y15A | 0.3 | 0/2[a] |
| Y17A | 0.65 | 1/2 |
| Y15A/N38D | 0 | 0/2[a] |
| Y17A/N38D | 1.25 | 0/2[a] |

[a]Animals did not show signs of streptococcal toxic shock syndrome, but rather, remained healthy Additional Mutants The invention has been described with reference to various specific and preferred embodiments and techniques. However, it should be understood that many variations and modifications may be made while remaining within the spirit and scope of the invention.

All publications and patent applications in this specification are indicative of the level of ordinary skill in the art to which this invention pertains. All publications and patent applications are herein incorporated by reference to the same extent as if each individual publication or patent application was specifically and in individually indicated by reference.

What is claimed is:

1. A composition comprising an isolated Streptococcal pyrogenic exotoxin type C (SPE-C toxin) comprising an amino acid substitution at aspartic acid-12 of SEQ ID NO: 2, and a carrier.

2. A composition comprising an isolated Streptococcal pyrogenic exotoxin type C (SPE-C) toxin, comprising substitution of alanine for aspartic acid-12 of SEQ ID NO: 2, and a carrier.

3. A composition comprising an isolated Streptococcal pyrogenic exotoxin type C (SPE-C toxin) comprising an amino acid substitution at asparagine-38 of SEQ ID NO: 2, and a carrier.

4. A composition comprising an isolated Streptococcal pyrogenic exotoxin type C (SPE-C) toxin, comprising substitution of aspartic acid for asparagine-38 of SEQ ID NO: 2, and a carrier.

5. A composition comprising an isolated Streptococcal pyrogenic exotoxin type C (SPE-C toxin) comprising an amino acid substitution at tyrosine-15 of SEQ ID NO: 2 and at asparagine-38 of SEQ ID NO: 2, and a carrier.

6. A composition comprising an isolated Streptococcal pyrogenic exotoxin type C (SPE-C) toxin, comprising substitution of serine or alanine for tyrosine-15 of SEQ ID NO: 2 and aspartic acid for asparagine-38 of SEQ ID NO: 2, and a carrier.

7. A composition comprising an isolated Streptococcal pyrogenic exotoxin type C (SPE-C) toxin, comprising substitution of serine for tyrosine-15 of SEQ ID NO: 2 and serine for asparagine-38 of SEQ ID NO: 2, and a carrier.

8. A composition comprising an isolated Streptococcal pyrogenic exotoxin type C (SPE-C) toxin, comprising an amino acid substitution at tyrosine-15 of SEQ ID NO: 2, asparagine-38 of SEQ ID NO: 2, and histidine-35 of SEQ ID NO: 2, and a carrier.

9. A composition comprising an isolated Streptococcal pyrogenic exotoxin type C (SPE-C) toxin, comprising substitution of alanine for tyrosine-15 of SEQ ID NO: 2, alanine for histidine-35 of SEQ ID NO: 2, and aspartic acid for asparagine-38 of SEQ ID NO: 2, and a carrier.

10. A composition comprising an isolated Streptococcal pyrogenic exotoxin type C (SPE-C toxin) comprising an amino acid substitution at tyrosine-17 of SEQ ID NO: 2 and at asparagine-38 of SEQ ID NO: 2, and a carrier.

11. A composition comprising an isolated Streptococcal pyrogenic exotoxin type C (SPE-C) toxin, comprising substitution of serine or alanine for tyrosine-17 of SEQ ID NO: 2 and aspartic acid for asparagine-38 of SEQ ID NO: 2, and a carrier.

12. A composition comprising an isolated Streptococcal pyrogenic exotoxin type C (SPE-C) toxin, comprising substitution of serine for tyrosine-17 of SEQ ID NO: 2 and serine for asparagine-38 of SEQ ID NO: 2, and a carrier.

13. A composition comprising an isolated Streptococcal pyrogenic exotoxin type C (SPE-C toxin) comprising an amino acid substitution at tyrosine-15 of SEQ ID NO: 2, at histidine-35 of SEQ ID NO: 2, and at asparagine-38 of SEQ ID NO: 2, and a carrier.

14. A composition comprising an isolated Streptococcal pyrogenic exotoxin type C (SPE-C) toxin, comprising substitution of alanine for tyrosine-15 of SEQ ID NO: 2, alanine for histidine-35 of SEQ ID NO: 2, and aspartic acid for asparagine-38 of SEQ ID NO: 2, and a carrier.

15. A composition comprising an isolated Streptococcal pyrogenic exotoxin type C (SPE-C toxin) comprising an amino acid substitution at aspartic acid-12 of SEQ ID NO: 2, at tyrosine-15 of SEQ ID NO: 2, at tyrosine-17 of SEQ ID NO: 2, at histidine-35 of SEQ ID NO: 2, at asparagine-38 of SEQ ID NO: 2, or at up to three of these amino acids of SEQ ID NO: 2, and a carrier.

16. A composition comprising an isolated Streptococcal pyrogenic exotoxin type C (SPE-C) toxin, comprising substitution of alanine for tyrosine-15 of SEQ ID NO: 2, and a carrier.

17. An isolated Streptococcal pyrogenic exotoxin type C comprising an amino acid substitution at aspartic acid-12 of SEQ ID NO: 2, at tyrosine-15 of SEQ ID NO: 2, at tyrosine-17 of SEQ ID NO: 2, at histidine-35 of SEQ ID NO: 2, or at asparagine-38 of SEQ ID NO: 2;

wherein the isolated Streptococcal pyrogenic exotoxin type C is 99% identical to SEQ ID NO: 2; and the isolated Streptococcal pyrogenic type C has reduced toxicity compared with wild-type.

18. The isolated Streptococcal pyrogenic exotoxin type C of claim 17, comprising substitution at tyrosine-15 of SEQ ID NO: 2, at histidine-35 of SEQ ID NO: 2, and at asparagine-38 of SEQ ID NO: 2.

19. The isolated Streptococcal pyrogenic exotoxin type C of claim 18, comprising substitution of tyrosine-15 of SEQ ID NO: 2 with alanine, histidine-35 of SEQ ID NO: 2 with alanine, and asparagine-38 of SEQ ID NO: 2 with asparate.

20. The isolated Streptococcal pyrogenic exotoxin type C of claim 17, comprising substitution at tyrosine-15 of SEQ ID NO: 2 and at asparagine-38 of SEQ ID NO: 2.

21. The isolated Streptococcal pyrogenic exotoxin type C of claim 20, comprising substitution of tyrosine-15 of SEQ ID NO: 2 with alanine and asparagine-38 of SEQ NO: 2 with aspartate.

\* \* \* \* \*